(12) United States Patent
Barrett et al.

(10) Patent No.: US 6,549,820 B1
(45) Date of Patent: Apr. 15, 2003

(54) METHOD AND SYSTEM FOR PROVIDING FEEDBACK FROM A NON-DESTRUCTIVE INSPECTION OF A COMPOSITE PART

(75) Inventors: Russell A. Barrett, Douglass, KS (US); Jon J. Fischer, Bentley, KS (US); Kenneth E. Garrett, Wichita, KS (US); David M. Gayle, Douglass, KS (US); Timothy L. Holdeman, Halstead, KS (US); Darrell C. Jundt, Derby, KS (US); Brian R. Kitt, Wichita, KS (US); Donald D. Ruebke, Whitewater, KS (US); Brett E. Russell, Seattle, WA (US); Kenneth C. Stewart, Wichita, KS (US); John M. Welch, Wichita, KS (US); Sandra L. Jansen, Wichita, KS (US)

(73) Assignee: The Boeing Company, Seattle, WA (US)

( * ) Notice: Subject to any disclaimer, the term of this patent is extended or adjusted under 35 U.S.C. 154(b) by 0 days.

(21) Appl. No.: 09/361,666

(22) Filed: Jul. 27, 1999

Related U.S. Application Data

(60) Provisional application No. 60/094,890, filed on Jul. 31, 1998.

(51) Int. Cl.[7] .............................................. G06F 19/00
(52) U.S. Cl. ........................ 700/110; 700/169; 382/141
(58) Field of Search ................................. 700/109, 108, 700/110, 111, 222, 279, 162, 182, 195, 121, 169, 173, 175; 702/84, 179, 82, 81; 705/3; 382/141; 73/611, 633, 628; 345/790

(56) References Cited

U.S. PATENT DOCUMENTS

| | | | |
|---|---|---|---|
| 4,141,347 A | 2/1979 | Green et al. ................ 600/441 |
| 4,649,380 A | 3/1987 | Penna ......................... 345/670 |
| 4,872,130 A | 10/1989 | Pagano ........................ 702/39 |
| 5,027,110 A | 6/1991 | Chang et al. ................ 345/668 |
| 5,042,305 A | 8/1991 | Takishita ....................... 73/625 |
| 5,088,045 A | * 2/1992 | Shimanaka et al. .......... 700/110 |
| 5,146,556 A | 9/1992 | Hullot et al. ................. 345/790 |
| 5,293,326 A | 3/1994 | Arima et al. .................. 702/39 |
| 5,459,410 A | 10/1995 | Henley |
| 5,475,613 A | 12/1995 | Itoga et al. .................... 702/39 |
| 5,541,846 A | * 7/1996 | Secrest ........................ 700/110 |
| 5,568,263 A | 10/1996 | Hanna ......................... 356/668 |
| 5,608,814 A | 3/1997 | Gilmore et al. .............. 382/141 |
| 5,619,429 A | 4/1997 | Aloni et al. .................. 700/279 |
| 5,640,199 A | 6/1997 | Garakani et al. .............. 348/87 |
| 5,655,084 A | 8/1997 | Pinsky et al. .................. 705/3 |
| 5,706,213 A | 1/1998 | Takakura et al. ............ 700/222 |
| 5,734,742 A | 3/1998 | Asaeda et al. ............... 382/141 |
| 6,259,960 B1 | * 7/2001 | Inokuchi ...................... 700/110 |
| 6,314,379 B1 | * 11/2001 | Hu et al. ....................... 702/81 |

* cited by examiner

Primary Examiner—Leo Picard
Assistant Examiner—Kidest Bahta
(74) Attorney, Agent, or Firm—Christensen O'Connor Johnson Kindness PLLC

(57) ABSTRACT

A computer-implemented method for providing on-line ultrasonically scanned images of composite parts for immediate feedback in a manufacturing environment is discussed. The scanned images are edited to indicate each deficiency that has been repaired on a previously assembled composite part. Quality assurance personnel enter data associated with each composite part and verify the data content. Repair personnel enter data associated with correcting an identified deficiency of the composite part. Historical data suitable for developing statistics and trends are stored for each type of composite part. When queries are launched, the statistical and trend data is filtered to produce reports that are displayed. That is, reports are generated that identify particular statistics and trends. The scan image and data associated with a composite part are linked together for cross-referencing and stored in a database that is accessible by client and server computers on a network. Images produced by an ultrasonic scanner(s) coupled to the network are stored for retrieval.

26 Claims, 34 Drawing Sheets

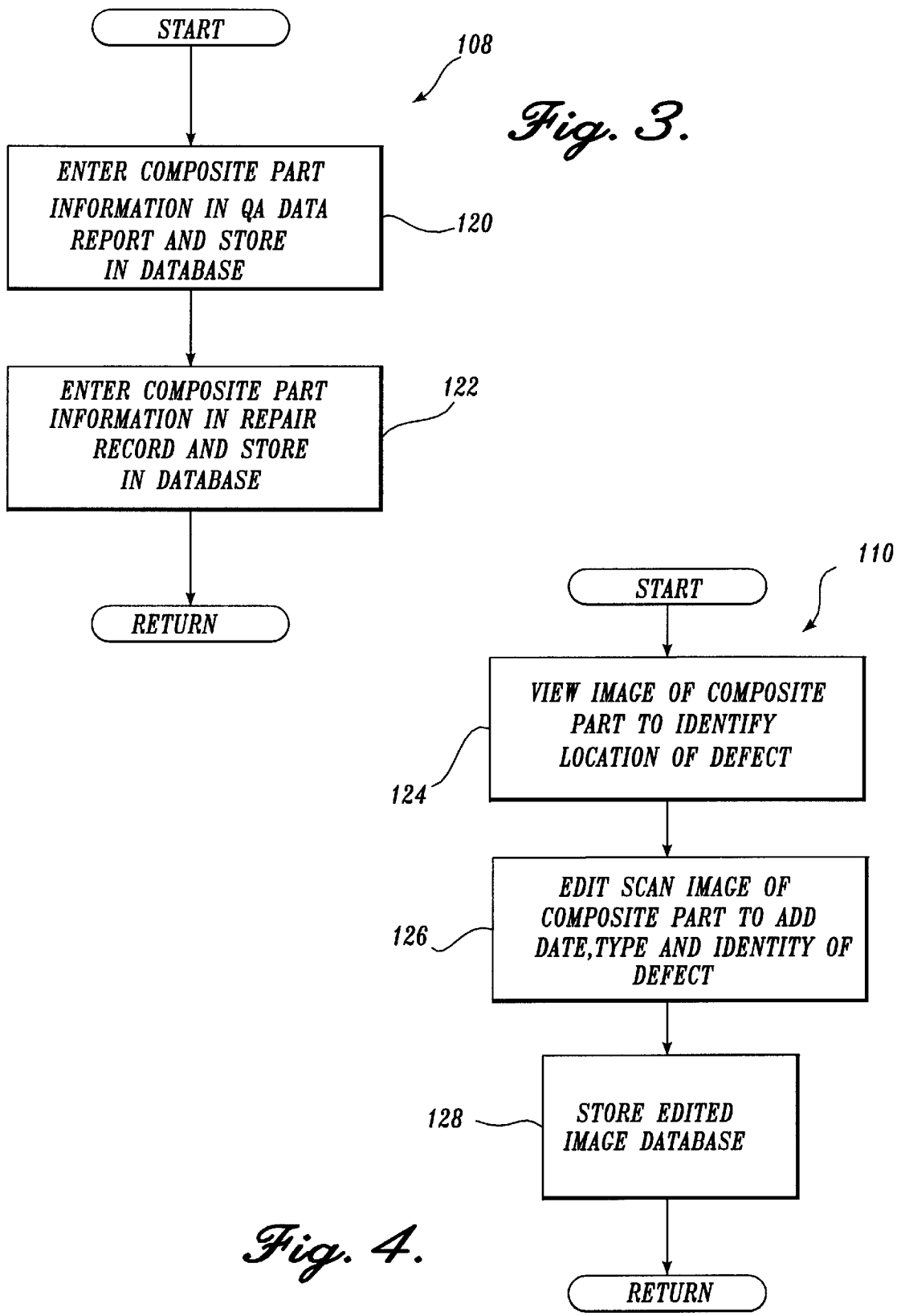

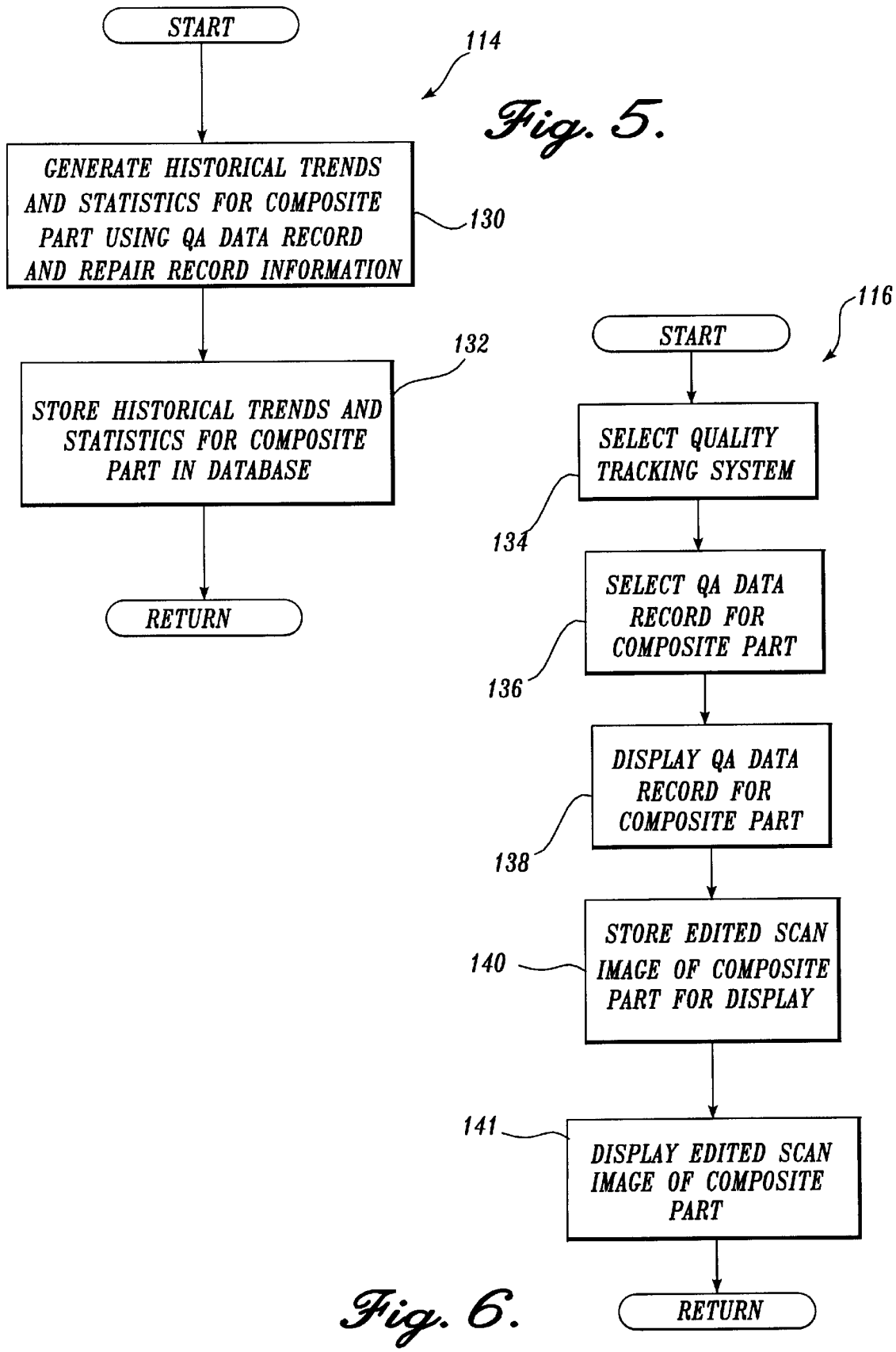

Fig. 9A.

| HISTORY OF PREVIOUSLY INSPECTED TKR #: SELECT QUERY | | | | | | | | |
|---|---|---|---|---|---|---|---|---|
| INSP. # | TKR # | DATE | PASS | RECORD | NCR # | IMAGE 1 | IMAGE 2 | SCAN # | DATA FILE # |
| 1 | 301260 | 3/01/99 | NO | 101 | 303617E | 301260 | N/A | 313W3110-9 | 301260 |
| 2 | 301260 | 3/15/99 | NO | 102 | 303617E | 301260RWK-3-15-99 | N/A | 313W3110-9 | 301260RWK-3-15-99 |
| 3 | 301260 | 3/20/99 | YES | 103 | N/A | 301260RWK-3-20-99 | N/A | 313W3110-9 | 301260RWK-3-20-99 |

RECORD: |◄| ◄ | 1 | ► | ►| | ►* OF 13

Fig. 10.

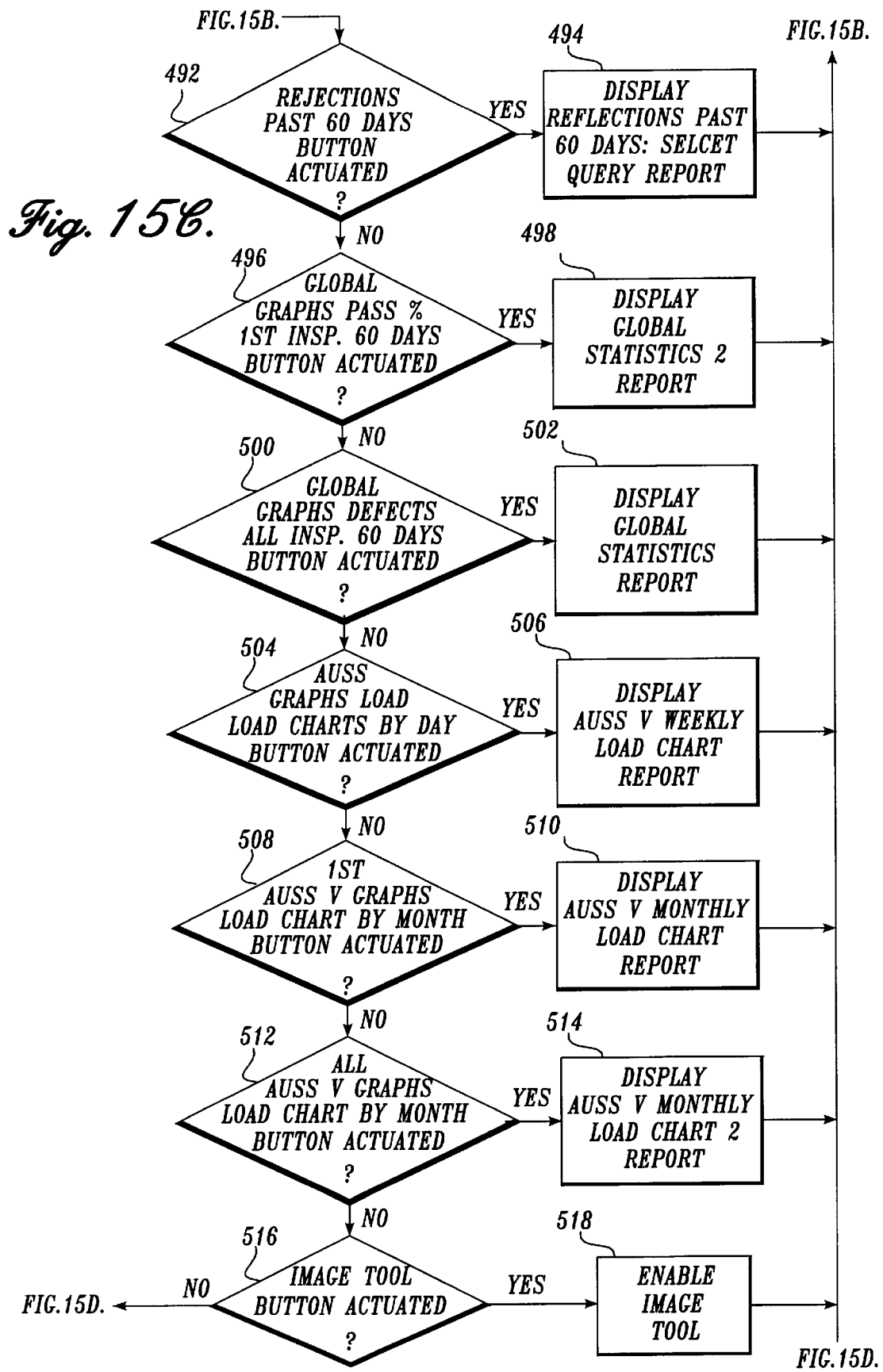

PART TREND2: SELECT QUERY

| PRODUCT NAME | DASH # | TKR | DATE | PASS | AUSS V NCI |
|---|---|---|---|---|---|
| 315W1527 | 54 | 200314 | 1/28/99 | NO | 951816E |
| ▶ 315W1527 | 54 | 200385 | 1/28/99 | NO | 402816E |

RECORD: |◀◀| |◀|  2  |▶| |▶▶| |▶*| OF 2

*Fig. 21.*

PERCENT: SELECT QUERY

| PASS FIRST TIME | PERCENT PASS |
|---|---|
| ▶ 315W1527 | 0.00% |

RECORD: |◀◀| |◀|  1  |▶| |▶▶| |▶*|

*Fig. 22.*

AUSS V RUN: SELECT QUERY

| MACHINE | DATE | TKR | PRODUCT NAME | DASH # | REJECT # |
|---|---|---|---|---|---|
| ▶ AUSSV #1 | 1/29/99 | 200395 | 314W3012 | 1 | N/A |
| AUSSV #1 | 1/29/99 | 200314 | 315W1527 | 54 | 951816E |
| AUSSV #1 | 1/28/99 | 200385 | 315W1527 | 54 | 402816E |

RECORD: |◀◀| |◀|  1  |▶| |▶▶| |▶*| OF 3

*Fig. 23.*

PART TREND: SELECT QUERY

| PRODUCT NAM | DASH # | TKR | PASS | DATE | AUSS V NCI | REPAIR NCR # |
|---|---|---|---|---|---|---|
| ▶ 315W1527 | 54 | 200314 | NO | 1/28/99 | 951816E | 951816E |
| 315W1527 | 54 | 200385 | NO | 1/28/99 | 402816E | 402816E |

RECORD: |◀◀| |◀|  2  |▶| |▶▶| |▶*| OF 2

*Fig. 24.*

| GLOBALPERCENTFIRST: SELECT QUERY | | | | | |
|---|---|---|---|---|---|
| PRODUCT NAME | PASS | TOTAL RUN | PERCENT PASS | PERCENTAGE OF ALL INSPECTED | LAST 60 DAYS |
| 315W3108 | 0 | 1 | 0.00% | 1.30% | 3/16/99 |
| 315W1527 | 0 | 3 | 0.00% | 3.90% | 3/16/99 |
| 313W3110 | 0 | 1 | 0.00% | 1.30% | 3/1/99 |
| 315A2102 | 0 | 2 | 0.00% | 2.60% | 2/15/99 |
| 315W1102 | 1 | 4 | 25.00% | 5.19% | 2/11/99 |
| 315W1101 | 2 | 4 | 50.00% | 5.19% | 3/13/99 |
| 314W3327 | 2 | 3 | 66.67% | 3.90% | 3/20/99 |
| 314T4111 | 13 | 16 | 81.25% | 20.78% | 3/7/99 |
| 315T3564 | 19 | 23 | 82.61% | 29.87% | 3/9/99 |
| 313W1121 | 1 | 1 | 100.00% | 1.30% | 3/19/99 |
| 313W1131 | 1 | 1 | 100.00% | 1.30% | 3/19/99 |
| 314N3012 | 2 | 2 | 100.00% | 2.60% | 3/9/99 |
| 314N3111 | 1 | 1 | 100.00% | 1.30% | 2/20/99 |
| 314W1112 | 1 | 1 | 100.00% | 1.30% | 3/19/99 |
| 314W1321 | 1 | 1 | 100.00% | 1.30% | 3/19/99 |

RECORD: 1 OF 23

Fig. 25.

| GLOBALPERCENTALL1STINSP: SELECT QUERY | | | | | |
|---|---|---|---|---|---|
| PART NUMBER | # PASS | TOTAL INSP | PERCENT PASS | PERCENTAGE OF ALL INSP | LAST INSP. |
| 141A6903-5 | 1 | 2 | 50.00% | 0.17% | 7/27/99 |
| 141A6903-6 | 1 | 1 | 100.00% | 0.08% | 7/4/99 |
| 311W1531-1 | 20 | 21 | 95.24% | 1.76% | 6/30/99 |
| 311W1531-2 | 22 | 23 | 95.65% | 1.92% | 7/2/99 |
| 311W3532-10S/R | 1 | 1 | 100.00% | 0.08% | 4/16/99 |
| 311W3532-9 | 1 | 1 | 100.00% | 0.08% | 4/17/99 |
| 311W3532-9S/R | 1 | 1 | 100.00% | 0.08% | 4/16/99 |
| 313A2111-1 | 32 | 35 | 91.43% | 2.93% | 8/9/99 |
| 313A2121-0 | 1 | 1 | 100.00% | 0.08% | 5/1/99 |
| 313A2121-1 | 16 | 19 | 84.21% | 1.59% | 5/10/99 |
| 313A2121-2 | 18 | 18 | 100.00% | 1.51% | 5/10/99 |
| 313A2231-3 | 9 | 10 | 90.00% | 0.84% | 5/20/99 |
| 313A2231-4 | 11 | 11 | 100.00% | 0.92% | 6/2/99 |
| 313U2112-910 | 33 | 35 | 94.29% | 2.93% | 7/10/99 |
| 313U2113-12S/R | 1 | 1 | 100.00% | 0.08% | 4/8/99 |

RECORD: |◀|◀| 1 |▶|▶|*| OF 286

| FIRSTINSPECTIONPASSPERCENTBYMONTH: SELECT QUERY | | | | | |
|---|---|---|---|---|---|
| PART NUMBER | # PASS | TOTAL INSP | PERCENT PASS | % OF ALL INSPECTE | LAST DATE INSP |
| 141A6903-5 | 1 | 2 | 50.00% | 0.17% | 7/29/99 |
| 141A6903-6 | 1 | 1 | 100.00% | 0.08% | 7/4/99 |
| 311W1531-2 | 1 | 1 | 100.00% | 0.08% | 7/2/99 |
| 313A2111-1 | 9 | 9 | 100.00% | 0.75% | 7/31/99 |
| 313U2112-910 | 1 | 1 | 100.00% | 0.08% | 7/10/99 |
| 313U2113-912 | 3 | 3 | 100.00% | 0.25% | 7/11/99 |
| 313U2114-911 | 7 | 7 | 100.00% | 0.59% | 7/25/99 |
| 313U2201-967 | 1 | 1 | 100.00% | 0.08% | 7/6/99 |
| 313U2201-968 | 1 | 1 | 100.00% | 0.08% | 7/15/99 |
| 313U2201-971 | 4 | 4 | 100.00% | 0.33% | 7/29/99 |

RECORD: 1 OF 157

| FIRSTINSPECTIONPASSPERCENTBYMONTH: SELECT QUERY | | | | | |
|---|---|---|---|---|---|
| PART NUMBER | # PASS | TOTAL INSP | PERCENT PASS | % OF ALL INSPECTE | LAST DATE INSP |
| 141A6903-5 | 1 | 2 | 50.00% | 0.32% | 7/29/99 |
| 141A6903-6 | 1 | 1 | 100.00% | 0.16% | 7/4/99 |
| 311W1531-2 | 1 | 1 | 100.00% | 0.16% | 7/2/99 |
| 313A2111-1 | 9 | 9 | 81.25% | 1.76% | 7/31/99 |
| 313U2112-910 | 1 | 1 | 100.00% | 0.48% | 7/10/99 |
| 313U2113-912 | 3 | 3 | 100.00% | 0.48% | 7/11/99 |
| 313U2114-911 | 7 | 7 | 100.00% | 1.12% | 7/25/99 |
| 313U2201-967 | 1 | 1 | 100.00% | 0.08% | 7/6/99 |
| 313U2201-968 | 1 | 1 | 100.00% | 0.08% | 7/15/99 |
| 313U2201-971 | 4 | 4 | 100.00% | 0.33% | 7/29/99 |
| 313U2201-972 | 3 | 3 | 100.00% | 0.48% | 7/25/99 |

RECORD: 1 OF 159

777 LINE (W) TREND FIRST INSPECTION PASS PERC...

| #PASS | TOTAL INSP | PERCENT PASS | MONTH |
|---|---|---|---|
| 1 | 3 | 33.33% | 1 |
| 7 | 10 | 70.00% | 2 |
| 41 | 59 | 69.49% | 3 |
| 242 | 293 | 82.59% | 4 |
| 342 | 407 | 84.03% | 5 |
| 333 | 428 | 77.80% | 6 |
| 308 | 371 | 83.02% | 7 |

RECORD: |◀◀|◀| 1 |▶|▶▶|▶*| OF 8

737NG LINE (A) TREND FIRST INSPECTION PASS PERCENTAGE: S...

| #PASS | TOTAL INSP | SUMOFCOUNTO | PERCENT PASS | MONTH |
|---|---|---|---|---|
| 1 | 3 | 3 | 33.33% | 2 |
| 4 | 6 | 6 | 66.67% | 3 |
| 32 | 43 | 43 | 74.42% | 4 |
| 82 | 89 | 89 | 92.13% | 5 |
| 36 | 45 | 45 | 80.00% | 6 |
| 75 | 80 | 80 | 93.75% | 7 |

RECORD: |◀◀|◀| 1 |▶|▶▶|▶*| OF 7

LINES OTHER THAN 777 OR 737NG TREND FIRST INSPECTION PASS P...

| #PASS | TOTAL INSP | PERCENT PASS | MONTH |
|---|---|---|---|
| 25 | 29 | 86.21% | 2 |
| 50 | 57 | 87.72% | 3 |
| 201 | 220 | 91.36% | 4 |
| 197 | 221 | 89.14% | 5 |
| 185 | 209 | 88.52% | 6 |
| 167 | 181 | 92.27% | 7 |

RECORD: |◀◀|◀| 1 |▶|▶▶|▶*| OF 7

*Fig. 28.*

| TOTAL FIRST INSPECTED PARTS - ALL SYS | MONTH |
|---:|---:|
| 3 | 1 |
| 42 | 2 |
| 122 | 3 |
| 544 | 4 |
| 711 | 5 |
| 676 | 6 |
| 625 | 5 |
| 178 | 6 |

RECORD: |◄◄| |◄| 1 |►| |►►| |►*| OF 8

| TOTAL INSPECTED PARTS - ALL SYSTEM | MONTH |
|---:|---:|
| 3 | 1 |
| 47 | 2 |
| 133 | 3 |
| 613 | 4 |
| 795 | 5 |
| 772 | 6 |
| 717 | 5 |
| 204 | 6 |

RECORD: |◄◄| |◄| 1 |►| |►►| |►*| OF 8

*Fig. 29.*

SELECT QUERY: PERCENTBAKE

| BAKE # | PASS | FIRST INSP. TOTAL | PASS% | LAST INSPECTION DATE |
|---|---|---|---|---|
| 7482 | 0 | 1 | 0.00% | 5/21/99 |
| 9926 | 0 | 1 | 0.00% | 5/10/99 |
| 9966 | 0 | 1 | 0.00% | 5/10/99 |
| 9902 | 0 | 2 | 0.00% | 5/8/99 |
| 9883 | 0 | 1 | 0.00% | 5/7/99 |
| 7389 | 0 | 1 | 0.00% | 5/5/99 |
| 9700 | 0 | 1 | 0.00% | 5/5/99 |
| 9572 | 0 | 1 | 0.00% | 4/28/99 |
| 8598 | 0 | 1 | 0.00% | 4/19/99 |
| 7264 | 0 | 1 | 0.00% | 4/14/99 |
| 7235 | 0 | 2 | 0.00% | 4/9/99 |
| 7210 | 0 | 1 | 0.00% | 4/6/99 |
| 7228 | 0 | 2 | 0.00% | 4/6/99 |

RECORD: 148 OF 431

AUSS#1 WEEKLY PASS PERCENTAGES: SELECT QUERY

| PASS ON AUSSY # | TOTAL INSPECTED | PASS PERCER | DATE FROM | DATE TO |
|---|---|---|---|---|
| 36 | 49 | 73% | 8/2/99 | 8/8/99 |

RECORD: 1 OF 1

AUSS#2 WEEKLY PASS PERCENTAGES: SELECT QUERY

| PASS ON AUSSY # | TOTAL INSPECTED | PASS PERCER | DATE FROM | DATE TO |
|---|---|---|---|---|
| 73 | 89 | 82% | 8/2/99 | 8/8/99 |

RECORD: 1 OF 1

Fig. 32.

REJECTIONS PAST 60 DAYS: SELECT QUERY

| DATE | NCR # | TKR # | INSP. # | LOG # | PART # | # OF DEFECTS | OTHER DEFEC | DEFECT TYPE FOU |
|---|---|---|---|---|---|---|---|---|
| 8/10/99 | 812921e | 108449 | 1 | 3278 | 315W1102-37 | | 2 | MISC |
| 8/10/99 | 623921e | 108067 | 1 | 3284 | 314W3111-171 | | 2 | MISC |
| 8/9/99 | 821621E | 201411 | 1 | 3271 | 314W1112-62 | | 1 | MISC |
| 8/8/99 | 202721E | 9815373 | 2 | 3247 | 313W3219-3S/R | | 2 | MISC |
| 8/8/99 | 470920e | 9813078 | 1 | 3253 | 315W1122-1 | | 1 | MISC |
| 8/8/99 | 480921e | 306606 | 1 | 3255 | 313W5121-1 | | 8 | MISC |

RECORD: 1 OF 286

METHOD AND SYSTEM FOR PROVIDING FEEDBACK FROM A NON-DESTRUCTIVE INSPECTION OF A COMPOSITE PART

CROSS REFERENCE TO RELATED APPLICATION

This application claims the benefit of Provisional Application Ser. No. 60/094,890, filed Jul. 31, 1998, the benefit of which is hereby claimed under 35 U.S.C. § 119. This provisional application is incorporated herein by reference.

FIELD OF THE INVENTION

The present invention relates to the inspection of parts and, more particularly, to the non-destructive inspection of parts.

BACKGROUND OF THE INVENTION

A fundamental step in the structural validation of parts, in particular assembled composite parts, is a thorough non-destructive inspection (NDI) of the part. The NDI inspection of composite parts occurs as one of the last steps in the production of a composite part. In many cases, in a production environment, NDI information identifying a deficiency may not be related back to the manufacturer of the components of the composite part or the crew assembling the part in time to correct the same deficiency in follow-on parts. Often, a relatively minor change in the components or techniques used to build a composite part can result in a positive NDI result, provided the change information is made available in a timely manner to the crew building the composite part.

In the past, the proprietary nature of various commercially available inspection systems that employ NDI techniques, e.g., Through Transmission Ultrasonic (TTU), Bond Tester, and Pulse Echo, has restricted efforts to rapidly or efficiently communicate NDI results to a crew building a composite part or a manufacturer of a defective component. In this regard, composite part manufacturers and NDI machines often employ incompatible computer systems. Such incompatible computer systems often require extensive software modifications in order for a manufacturer's computer system to exchange data with an NDI computer system and vice versa. As a result, in the past composite part manufacturers have often produced several parts requiring exactly the same rework before NDI information regarding the deficiency is provided to the manufacturer of composite part components or a crew assembling a composite part.

Prior efforts at sharing NDI results, with a crew building composite parts, have included the following: (1) the creation of a story board with hard copy prints of ultrasonic scan images of the parts; (2) weekly status reports summarizing percentages of first time ultrasonic scan discrepancies; and (3) crew meetings with the results of the ultrasonic scans read aloud to the crew and/or the information placed on a viewfoil and displayed using an overhead projector. Because ultrasonic scan results have been manually gathered, a significant lag time has occurred between the preparation and presentation of NDI results to the crew building the composite parts.

Since the assembly of composite parts is usually a sequential process, a deficiency identified by a NDI will continue to occur until the NDI results are presented to the crew assembling the composite parts, and corrective action is implemented. Although in the past NDI results eventually have been provided to the crew needing the information, a good deal of waste, rework, and possibly scrap has been incurred before the information is utilized. In the past, no adequate system for quickly and efficiently feeding back pertinent NDI results from the most recent builds of a composite part to the crew manufacturing the part has been available. Further, no adequate system for allowing an ultrasonic scan image to be accessed by the crew without a significant lag time to allow for the collection, preparation, and presentation of the image has been available. The present invention addresses the need for a method and a system that provides to a crew assembling composite parts timely feedback of the results of an NDI of previously assembled parts, so that changes necessary to correct a deficiency may be promptly performed on follow-on composite parts.

SUMMARY OF THE INVENTION

In accordance with this invention a computer-implementable method of rapidly and quickly providing NDI information to a crew building parts, particularly composite parts, hereinafter referred to as a Quality Tracking System, or QTS, is provided. The method comprises: gathering NDI information about the parts as they are manufactured; gathering other information, including repair information, about parts from manufacturing personnel; linking the NDI information to the other information; storing the linked NDI and other information in a database; and, upon user request, selectively deriving information about the parts from the information stored in the database; and displaying reports based on the derived information.

In accordance with other aspects of this invention, the gathering of NDI information comprises ultrasonically scanning the parts as they are manufactured in order to identify defects in the parts.

In accordance with further aspects of this invention, gathering other information, including repair information, about the parts includes providing an input window for manufacturing personnel to enter information regarding the identity of parts, defects in parts, and the repair of defects in the parts.

In accordance with yet other aspects of this invention, the computer-implementable method comprises collating the NDI and other information gathered about parts, including defects in the parts, based on user-initiated queries, and displaying the results of such collation.

In accordance with yet still further aspects of this invention, the results of the collation are displayed in tabular form.

In accordance with yet other aspects of this invention, the NDI and other information gathered about parts is used to produce graphs and other statistical data showing trends and other information about the parts.

As will be readily appreciated from the foregoing description, the invention provides a computer-implementable method of rapidly and quickly gathering NDI and other information about parts, particularly composite parts, as they are manufactured and providing the information to manufacturing and other personnel. Because defect and repair information is gathered on parts as they are manufactured, manufacturing process steps can be modified in real time in order to avoid or eliminate defects in subsequent composite parts as they are manufactured.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 is a functional flow diagram illustrating in more detail the enter data associated with composite part step included in FIG. 2;

FIG. 4 is a functional flow diagram illustrating in more detail the edit scan image to include data associated with the composite part step included in FIG. 2;

FIG. 5 is a functional flow diagram illustrating in more detail the generate composite part statistic and trend date step included in FIG. 2;

FIG. 6 is a functional flow diagram illustrating in more detail the display scan image of composite part step included in FIG. 2;

FIG. 9A is an exemplary quality assurance DATA RECORD window that enables a user to enter data associated with a composite part and display trends, statistics, and the scan image of the composite part;

FIG. 10 is an exemplary table that lists records in the Quality Tracking System that have the same composite manufacturing center tracking number (CMF TKR #) when a button in the quality assurance DATA RECORD form is selected by a user;

FIGS. 15B, 15C, and 15D are functional flow diagrams for FIG. 15A;

FIG. 21 is an exemplary table that lists first time inspection results that is displayed when a button in the quality assurance DATA RECORD window is selected by the user;

FIG. 22 is an exemplary table that lists the first time inspection results for the past 60 days that is displayed when a button in the quality assurance DATA RECORD window is selected by the user;

FIG. 23 is an exemplary table that lists all inspection results that is displayed when a button in the quality assurance DATA RECORD window is selected by the user;

FIG. 24 is an exemplary table that lists all inspection results that is displayed when a button in the REPAIR RECORD window is selected by a user;

FIG. 25 is an exemplary table that lists the global first time inspection pass percentages that is displayed when a button in the MORE QUERIES and other window is selected by a user;

FIG. 26 is an exemplary table listing the global percent first time pass percentages for all composite parts that is displayed when a button in the MORE QUERIES and other window is selected by a user;

FIG. 27 are exemplary tables listing the global first time inspection pass percentages for a given month entered by a keyboard and the global pass percentages for all inspections by the month that are displayed when a button in the MORE QUERIES and other window is selected by a user;

FIG. 28 are exemplary tables that list the first time inspection results for three separate production lines that are displayed when a button in the MORE QUERIES and other window is selected by a user;

FIG. 29 are exemplary tables that list the first time inspection results for all production models by the month and the total number of composite parts inspected for all production models by the month that are displayed when a button in the MORE QUERIES and other window is selected by a user;

FIG. 30 is an exemplary table that lists the pass percentages for autoclave baking that is displayed when a button in the MORE QUERIES and other window is selected by a user;

FIG. 31 are exemplary weekly machine pass percentage report that includes tables that list the results of inspections by an AUSS V machine and the results of inspections by another AUSS V machine that are displayed when a button in the MORE QUERIES and other window is selected by a user;

FIG. 32 is an exemplary rejections past 60 days input that includes a table that lists rejections of composite parts for the last 60 days when a button in the MORE QUERIES and other form is selected by a user.

DETAILED DESCRIPTION OF THE PREFERRED EMBODIMENT

Figure 1:
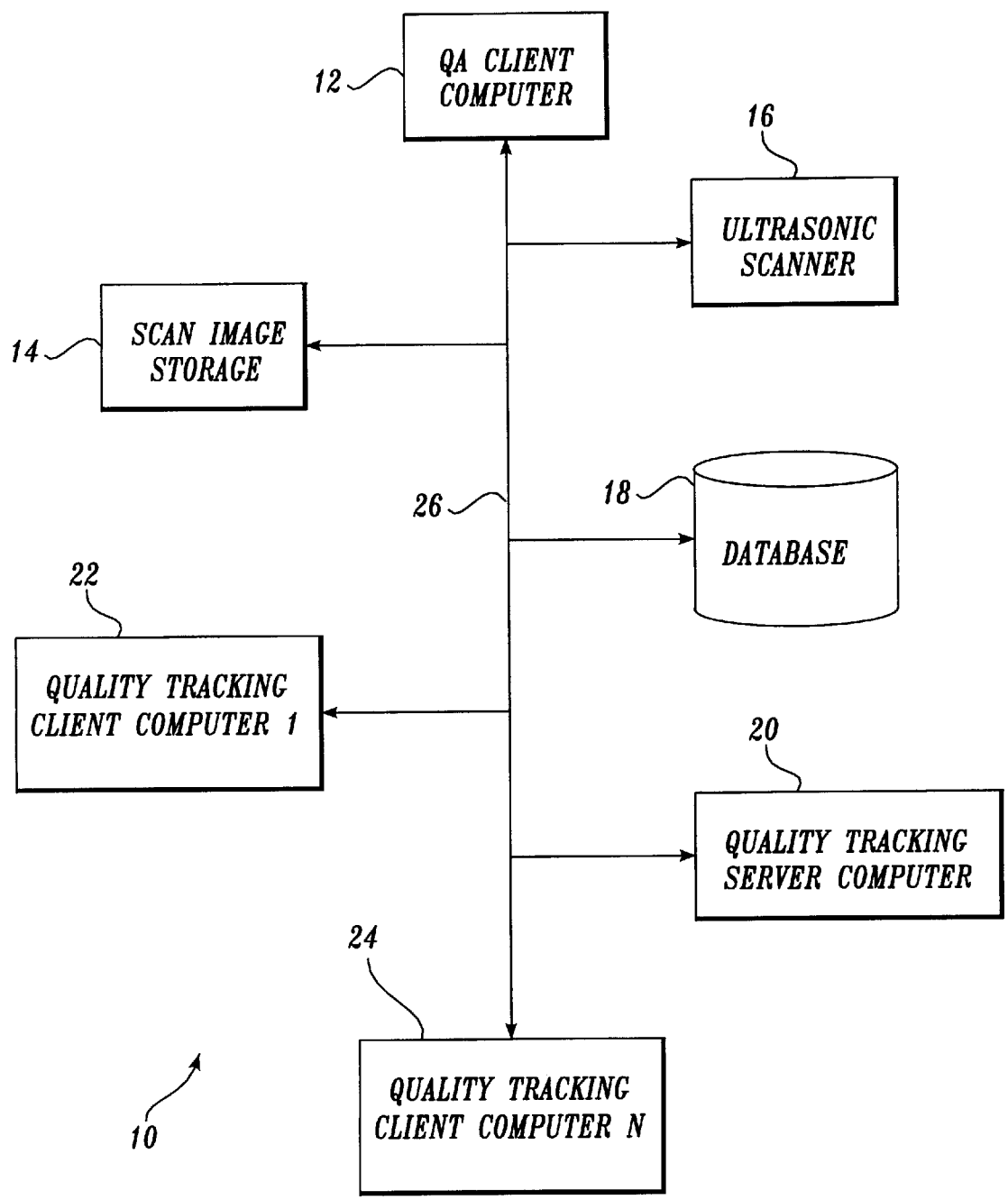
FIG. 1 is exemplary block diagram of a computer network suitable for implementing the present invention.

The present invention is directed to providing the timely transmittal of data produced by the Non-Destructive Inspection (NDI) of a part, particularly a composite part, in a manufacturing environment. The present invention is directed to reducing, if not entirely eliminating, the waste resulting from manufacturing personnel's lack of knowledge of existing or current deficiencies in the part. The NDI data is communicated using existing computing hardware and customized "off-the-shelf" software with discrete and coordinated input fields that document the part status and inspection results. As will be better understood from the following description, the present invention is designed to be used "on-line" and track the progress of part manufacturing performance over time. In effect, the present invention can be used to provide a living document about parts in a manufacturing environment, particularly composite parts. The present invention enables statistical data to be retrieved and provides support for future design and manufacturing choices.

As will also be better understood from the following description, the present invention enables users to view an ultrasonically produced image of a composite part, identify significant problems or anomalies in the part, and transmit the resulting information to other manufacturing personnel so that prompt corrective action can be taken. The invention avoids the disadvantages associated with word of mouth communication or rejection tag documents containing discrepancy descriptions. Preferably, a composite part image is produced by a scanning machine performing a Through Transmission Ultrasound (TTU) inspection of the part. The image may be viewed by personnel involved in the assembly, maintenance, or validation of the composite part. Composite part records for an entire product line are captured and stored for retrieval in a relatively short period of time by an on-line Quality Tracking System (QTS), formed in accordance with this invention. The QTS improves throughput in a manufacturing environment and provides the ability to track part manufacturing performance.

The present invention provides a computer-implementable method and a system that captures, stores, and retrieves ultrasonic inspection results of composite parts in an expeditious manner so that the "lessons learned" from one part can be applied to the very next build of the part. The QTS creates an on-line computerized database and is preferably implemented using personal computer (PC) based hardware and software. Because the hardware and software are preferably PC based, the invention is readily implemented using off-the-shelf software with designed and specific input fields. The hardware and software have the ability to create "real-time" associative pictures on a per-part basis based on an ultrasonic scan of a composite part. The scan image is viewable on a display device, e.g., a PC monitor, when accessed by manufacturing and other personnel. The software and hardware have the ability to store historical part record information and the software should have cross-tracking capability so that a "production order" can be tracked on a per-part basis. Preferably the software has on-line help/document features and on-line step-by-step instruction for usage. Local users' PC(s) can be interfaced via a Local Area Network (LAN) and remote users' PCs can be interfaced via a Wide Area Network (WAN) or the Internet.

The Quality Tracking System (QTS) data is partially derived from an ultrasonic inspection of a part using a suitable ultrasonic inspection device such as an automated TTU inspection system. First, the composite part is scanned by the automated TTU inspection system. All of the wetted area of a given part is swept so that every square inch of the part is included in the scan image. Typically, water is employed as the coupling agent for the ultrasonic waves in the wetted area. Quality Assurance personnel fill in specifically designed input fields with data associated with the composite part. At the time of data entry, the QTS "links" the scan image to the "designed input fields" so that they are cross-referenced to each other. Thereafter, preferably a system administrator, e.g., another Quality Assurance individual, verifies the content of the entered composite part data. Part record "trends" and statistics are automatically gathered from the "designed input fields" by the software based on user queries and suitable reports are displayed. The QTS is designed to be accessed by PCs located in the manufacturing areas, which allows the production records and scan images for previous composite parts to be immediately available to manufacturing personnel building the next composite part.

As will be better understood from the following description, the present invention enables users to access a pictorial image via a link between the designed input fields and a related scanned image. The link is created by a computer program that combines entered part data and scan image data. The link makes both accessible on-line in a manufacturing environment. The part input fields are designed to provide information pertinent to the part in terms of parameters that may influence the outcome for a given part. The input fields are designed to mesh with the captured and linked image so as to produce an inherently accurate record of the part.

One of the challenges for successfully producing a composite part in a production manufacturing environment is understanding the cause and effect of certain anomalies that may occur. Employing a QTS formed in accordance with this invention, and reviewing the composite part input fields, provides the high level of understanding required for the assembly of advanced composite parts.

A feature of a preferred embodiment of a QTS formed in accordance with this invention are the input fields that are available for comment. Data may be extracted from the comment input fields for future determination. The type of data requested or recorded in the input fields pertinent to the quality assessment of composite parts preferably include the following: Inspection Machine Number, Part Number, Process Specification, Requalification #, Scan Descriptions, Product Family, Scan Date, Part Record Number, Tool Type and Set, Scan Data File (as it is recorded on the Scanning System), Bake Number, Inspection Number, Image Name, Whether the part Passed, Non-Compliance Record Number, Defect Attenuation, Defect Location, Defect Size, Number of Defects, Repair Information, Part Trend Information, Comments Section, and Log Number reference as well as other traceable information.

The benefits of employing a Quality Tracking System formed in accordance with the invention include the following:

(1) detailed composite part record and traceability;

(2) reduced rework—the ability not to make the same mistake twice;

(3) reduced cost—rework/repair is one of the highest drivers in the cost to produce composite parts;

(4) increased quality—the ability to track and record data associated with the composite part improves quality;

(5) increased throughput—reduced repair and rework results in more composite parts delivered in a timely manner;

(6) schedule compliance;

(7) delivery capability—producing more composite parts on time allows a competitive advantage to deliver on commitments;

(8) positive feedback as well as corrective action feedback—morale is increased as successes mount and a string of composite parts consistently pass the ultrasonic scan inspection, and corrective action is recognized and acted upon more quickly; and (9) overall general composite part history—the QTS may be used for future designs, cost trade information, production facility justification, and PRR activity.

In one actual implementation, a QTS formed in accordance with this invention successfully recorded an impressive 90 percent average first time inspection pass rate for composite parts. A comparative analysis on composite parts that initially did not use the present invention revealed an approximate first time inspection pass rate of only 60 percent.

To further understanding of the following description of a preferred embodiment of this invention, the following list of abbreviations and acronyms is provided.

| | |
|---|---|
| AUSS V | Advanced Automated Ultrasonic Scanning System (Version 5) |
| CMF | Composite Manufacturing Facility |
| CMF TKR # | Composite Manufacturing Center Tracking Number |
| NCR # | Non Conformance Record Number |
| INSP. | Inspection or Inspections |
| OEE | Overall Equipment Effectiveness |
| QA | Quality Assurance |
| TIFF | Tagged Image File Format |
| BMP | Bitmap (Binary Mapped Pixels) Image Format |
| PO | Production Order |
| PRR | Program Review Requirements - engineering change activity |
| QTS | Quality Tracking System |

Preferred Embodiment

FIG. 1 is an exemplary block diagram illustrating a client-server architecture 10 suitable for implementing a QTS formed in accordance with this invention. In the following description, the term "server" is used interchangeably with the term "server computer," and the term "client" is used interchangeably with the term "client computer." The single quality tracking server 20 shown in FIG. 1 coupled to a network 26 may actually comprise a group of distributed servers to allow resource capacity to be scaled as necessary to efficiently administer the QTS. The use of distributed servers to administer the QTS provides dynamic scaling of resources to match the number of users accessing the system. The network 20 may be a local area network (LAN), a wide area network (WAN), the Internet, or combinations thereof.

The ultrasonic scanner 16 shown in FIG. 1 is a conventional automated ultrasonic scanner, such as a TTU scanner, that ultrasonically scans composite parts produced in a manufacturing environment and generates a related scan image. Other types of scanners, such as pulse echo (PE) scanners, for example, may also be employed. In any event, the output of the scanner 16 is coupled by the network 26 to a scan image storage 14 which stores the scan images produced by the ultrasonic scanner 16. Alternatively, the scan image storage may be part of the ultrasonic scanner 16.

One or more quality assurance (QA) client computers 12 coupled to the network 26 enables manufacturing personnel to enter data associated with a scan image. As a quality assurance client 12 enters associated data, the server 20 links the scan image to the associated data record and stores the linked data and the scan image in a database 18 that is also coupled to the network 26. The server 20 administers the database 18 for the QTS. As will be better understood from the following description, a plurality of quality tracking client computers 22 and 24 also coupled to the network 26 enable manufacturing and other personnel to access a pictorial display of a scan image and associated data linked to the image for previous and current composite parts. As will be better understood from the following description, the quality tracking client computers 22 and 24 also enable manufacturing and other personnel to query the information stored in the database 18 and obtain a variety of reports including statistical and trend reports in both graphical and tabular form. The quality assurance client computers 12 and the quality tracking client computers 22, 24 may be the same computers. The quality assurance client 12, storage 14, scanner 16, database 18, server 20, and quality tracking clients 22 and 24 may be positioned remotely from each other at disparate locations and exchange data and images with each other over the network 26.

Figure 2:
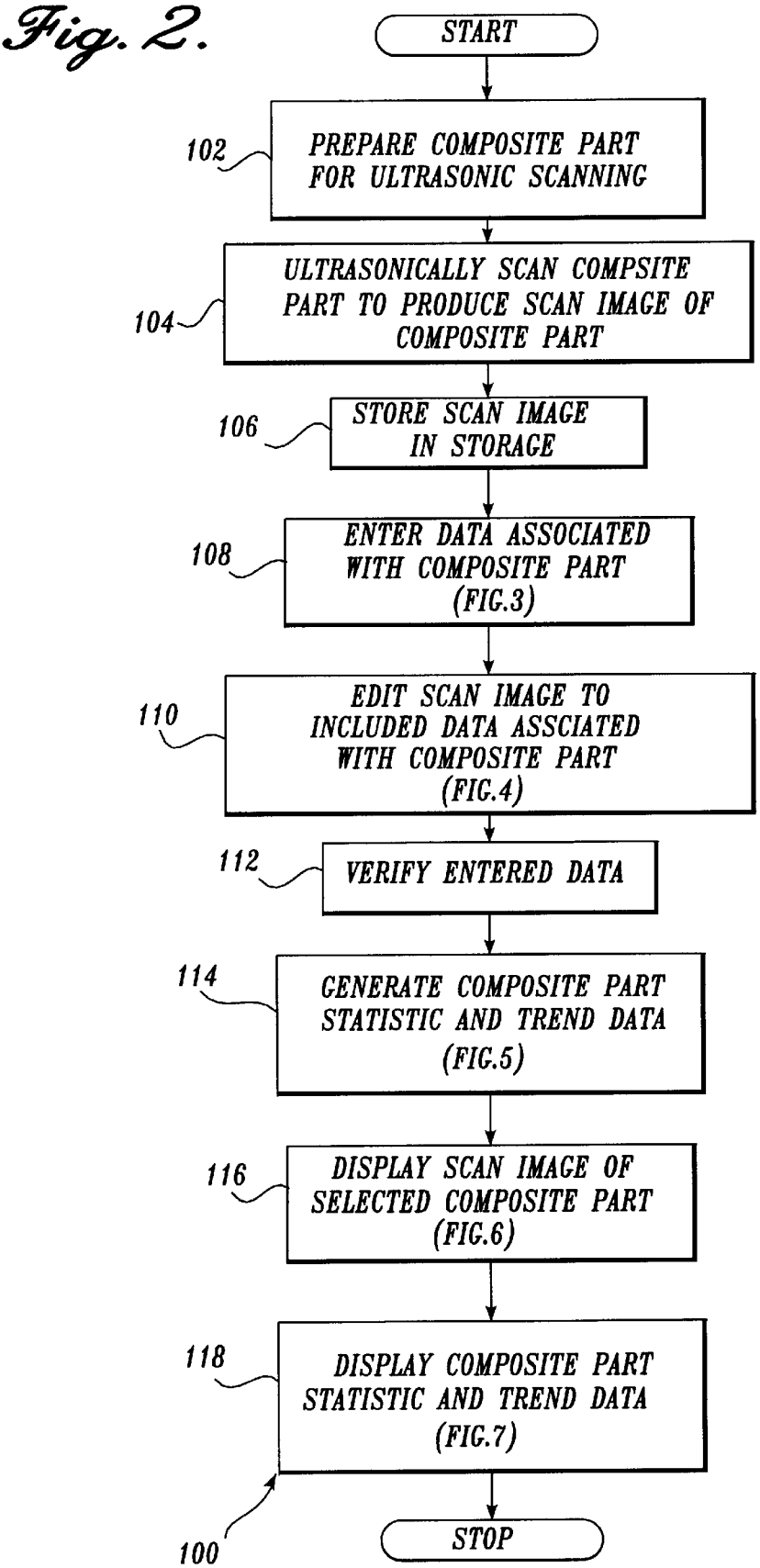
FIG. 2 is a functional flow diagram that shows an overview of the main logic flow of a Quality Tracking System (QTS) formed in accordance with this invention.

FIG. 2 is a high level functional flow diagram 100 that illustrates the steps implemented by the software included in a Quality Tracking System formed in accordance with this invention in a composite part manufacturing environment. Beginning at a start block, the logic flow advances to a block 102 where a selected composite part is prepared for ultrasonic scanning. This involves positioning the part with respect to an ultrasonic scanner and wetting the part with a suitable wetting agent such as water. The water serves to couple the TTU or other scanner to the composite part. The logic then shifts to a block 104 where the scanner 16 scans the composite part and produces one or more scan images thereof. (The part may be repositioned during scanning, if necessary.) The logic then advances to a block 106 where the scan image is stored in the scan image storage 14. Stepping to a block 108, the inspection data associated with the composite part is entered by quality assurance personnel and the entered data is linked to the scan image. At block 110, the scan image is edited, which adds associated data to the scan image, and the edited scan image is stored in the database 18. In block 112, the entered data associated with the composite part is displayed so that it can be verified by a quality assurance personnel. Obviously, blocks 104–112 are repeated as necessary.

The logic then shifts to a block 114 where composite part data is manipulated to produce statistic and trend data that is stored in the database 18. At block 116, at a user's request, the scan image of a composite part is retrieved from the database 18 and displayed. Moving to a block 118, the stored data is retrieved (at the user's request) and manipulated further, as necessary, to generate statistic and trend data for the composite parts whose data is stored in the database 18, which is then displayed. Thus, a user may select for display a specific edited scan image or statistics or trends, as well as other data, for the composite parts whose data is entered into the QTS. Next, the logic advances from block 118 to the end block.

FIG. 3 is a functional flow diagram that illustrates in more detail the data entry step (block 108) of FIG. 2. Beginning with a start block, the logic moves to a block 120 where quality assurance (QA) data for the part scanned (block 104, FIG. 2) is entered by quality assurance personnel. The QA data is entered via a window shown in FIG. 9A and described below. The QA DATA RECORD is stored in the database 18. Next, at block 122, repair data associated with the composite part (if any) is entered by repair personnel. The repair data is entered via a window illustrated in FIG.

11A and described below. Like the QA DATA RECORD, the repair data is stored in the database 18. Although not shown, if desired, other data associated with the inspection of the composite part may be entered via other windows and the resulting records stored in the database 18. The logic shown in FIG. 3 ends at block 122 and returns to the main logic flow illustrated in FIG. 2 (block 110).

Figure 33:
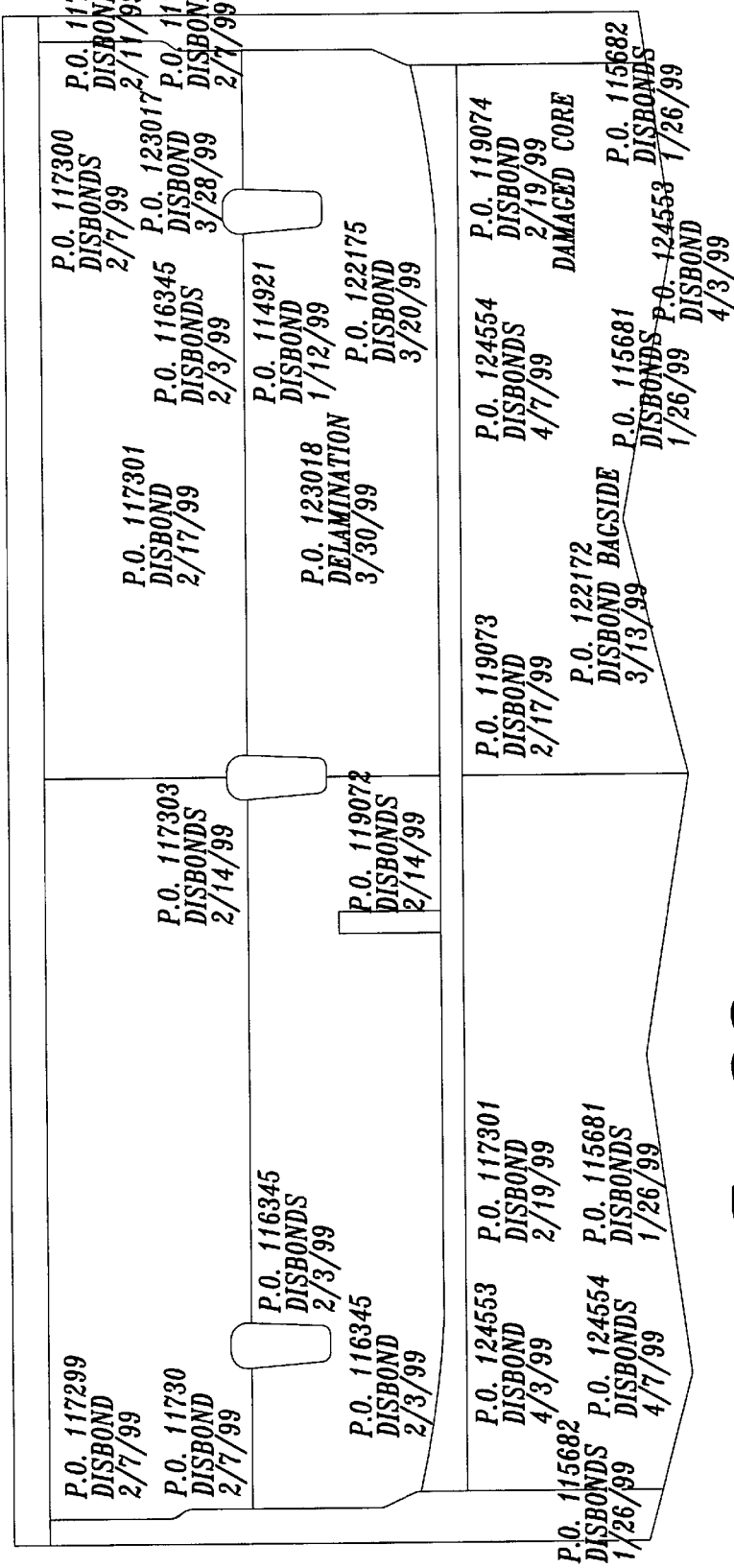
FIG. 33 is an exemplary image of a composite part created by ultrasonically scanning the part that has been edited to include the location, date, type and identifier for repairs made to the part.

FIG. 4 is a functional flow diagram that illustrates in more detail the scan image editing step (block 110) of FIG. 2). Moving from a start block, the logic steps to a block 124 where a user views the scan image of a composite part to identify the location of a defect. Next, at block 126, the displayed scan image is edited by adding a date, type, and alphanumeric identifier for the defect. Repair information may also be entered. FIG. 33 (described below) is an exemplary illustration of a scan image that has been edited in the manner illustrated in FIG. 4 and described above. Advancing to block 128, the edited image of the composite part is stored in the database 18. Next, the logic returns to the main logic flow shown in FIG. 2 (block 112).

FIG. 5 is a functional flow diagram that illustrates in more detail the generate composite part statistic and trend data step (block 114) of FIG. 2. Beginning at a start block, the logic moves to a block 130 where historical trends and statistical information for a composite part are derived from the QA DATA RECORD and REPAIR RECORD information, stored in the database 18. In essence, as will be better understood from the following discussion, the QA DATA RECORD and REPAIR RECORD information is collated and manipulated so that it can be quickly displayed in graphic or tabular from based on a user request. Next, at block 132, the generated historical trends and statistical information for the composite part are stored in the database 18. The logic then returns to the main logic flow shown in FIG. 2 (block 116).

Figure 8A:
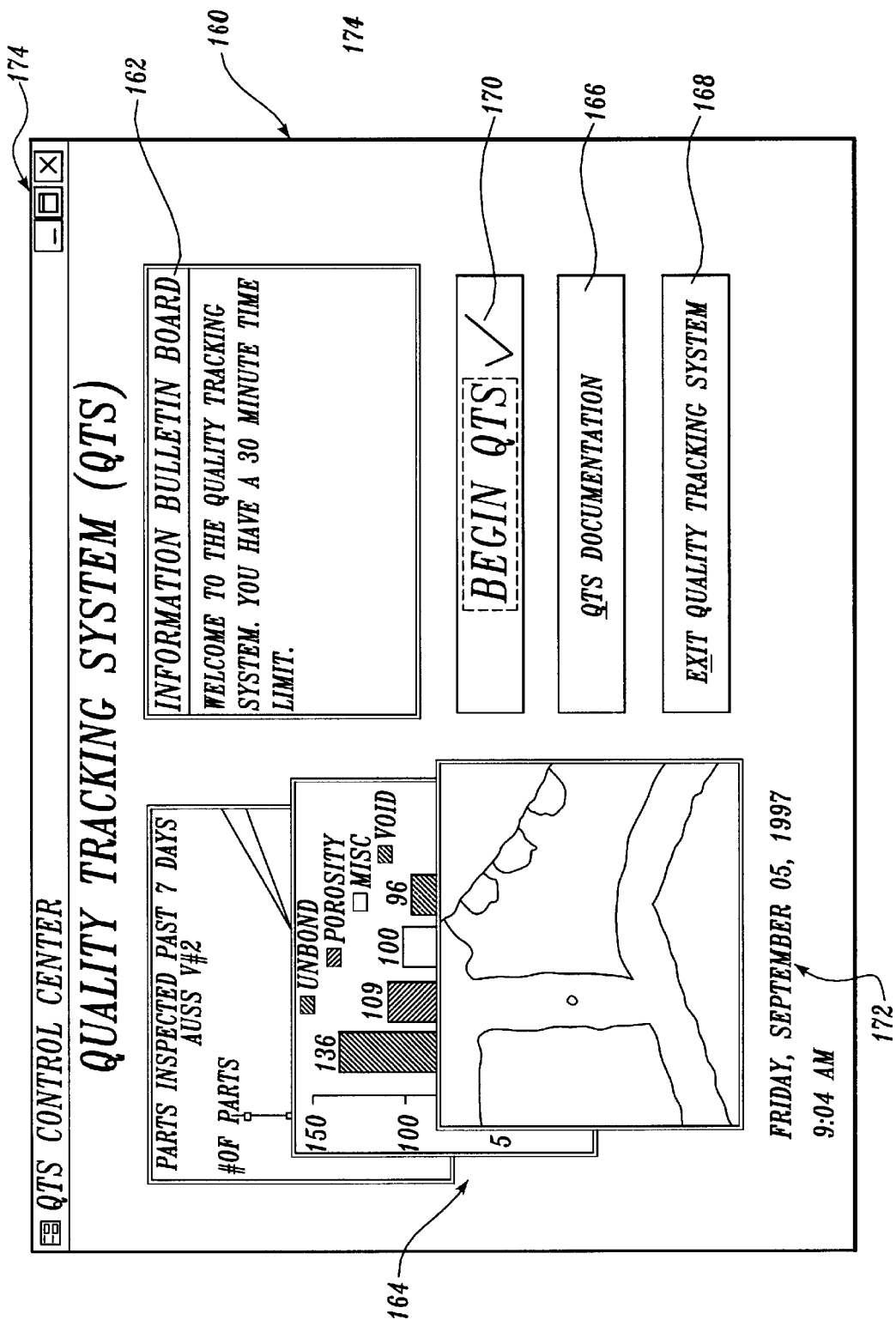
FIG. 8A is an exemplary QTS control center window that enables a user to select options.

FIG. 6 is a functional flow diagram that illustrates in more detail the display scan image of selected composite part step (block 116) of FIG. 2. Beginning at a start block, the logic advances to a block 134 where the QTS is selected by a user. A QTS control center window that enables a user to select the QTS is shown in FIG. 8A and described below. Next, at block 136, the user selects the QA DATA RECORD for a composite part to be displayed. In response, at block 138, the QA DATA RECORD for the composite part is displayed. Moving to block 140, after a QA DATA RECORD has been displayed, a user can select the edited scan image of a composite part for display. In response, at block 141, the edited scan image of the composite part is displayed. Then the logic returns to the main logic flow shown in FIG. 2 (block 118).

Figure 7:
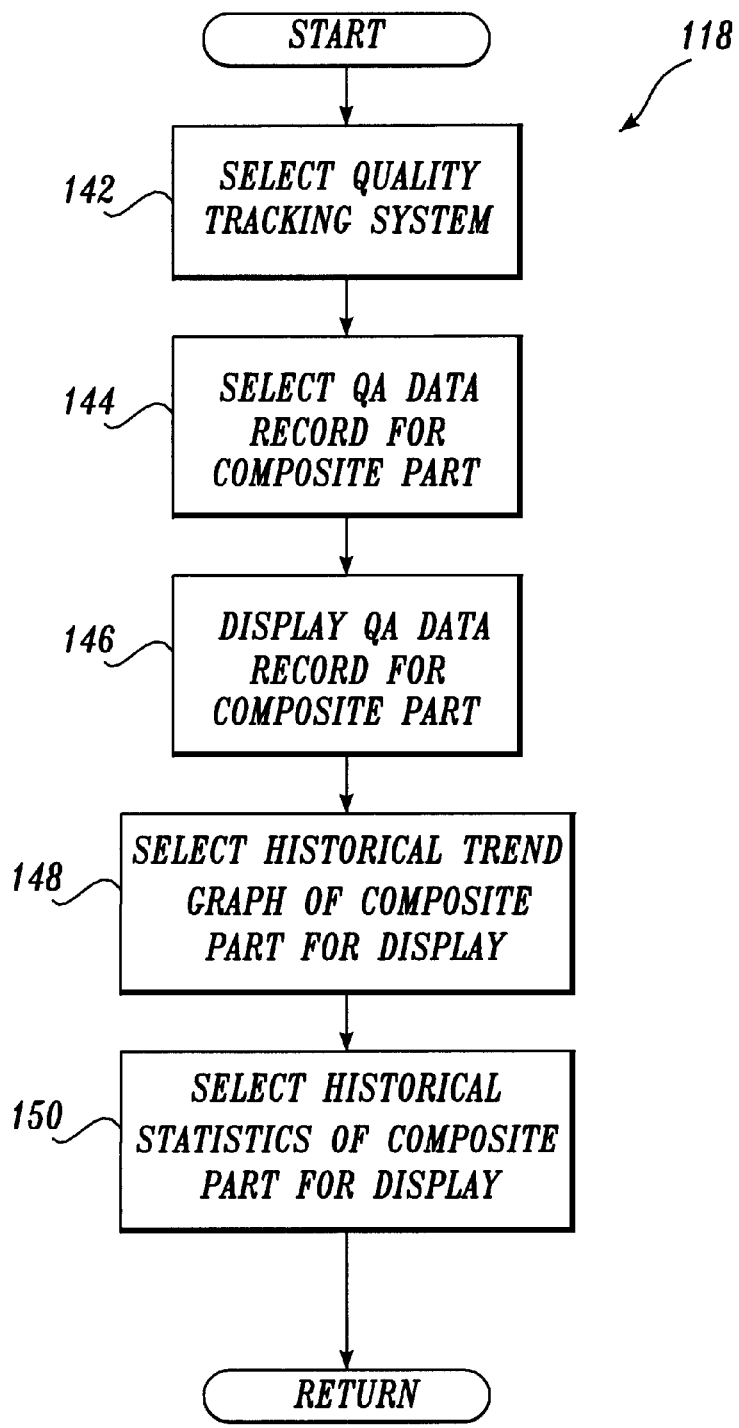
FIG. 7 is a functional flow diagram illustrating in more detail the display composite part statistic and trend data step included in FIG. 2.
Figure 9A:
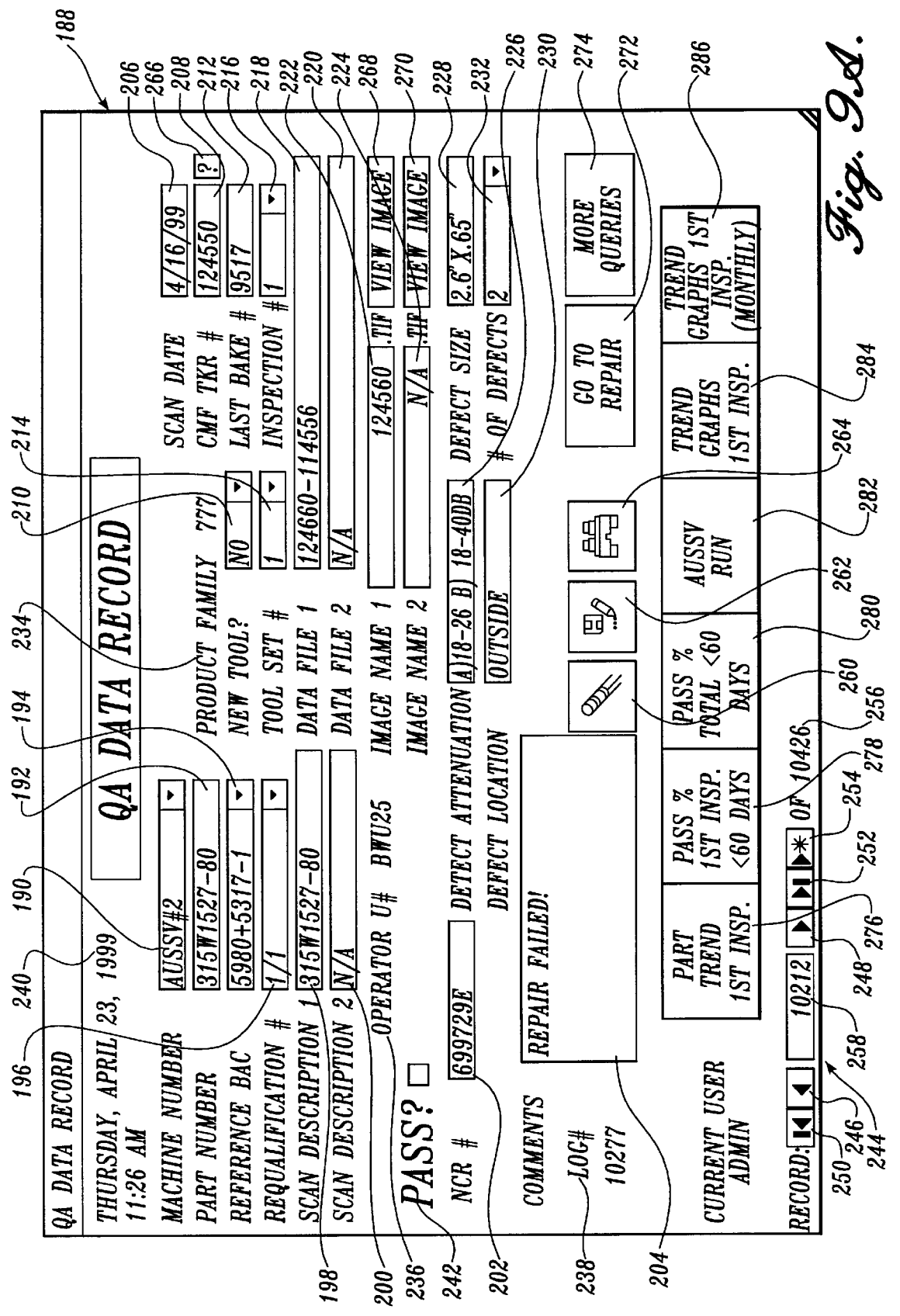
Figure 11A:
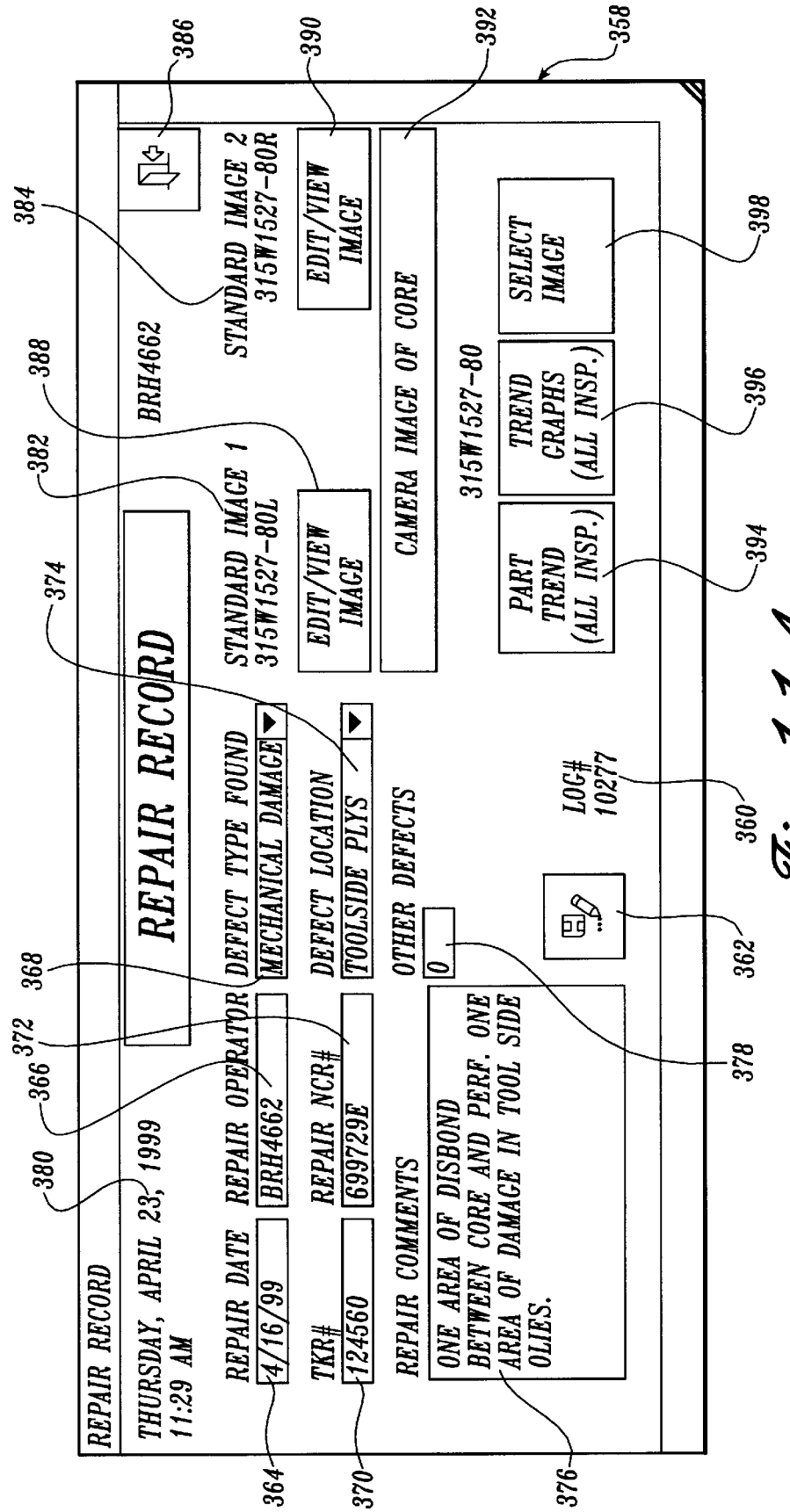
FIG. 11A is an exemplary REPAIR RECORD window that enables a user to enter data associated with a repair of a composite part and display trends, statistics, and the scan image of the composite part.
Figure 15A:
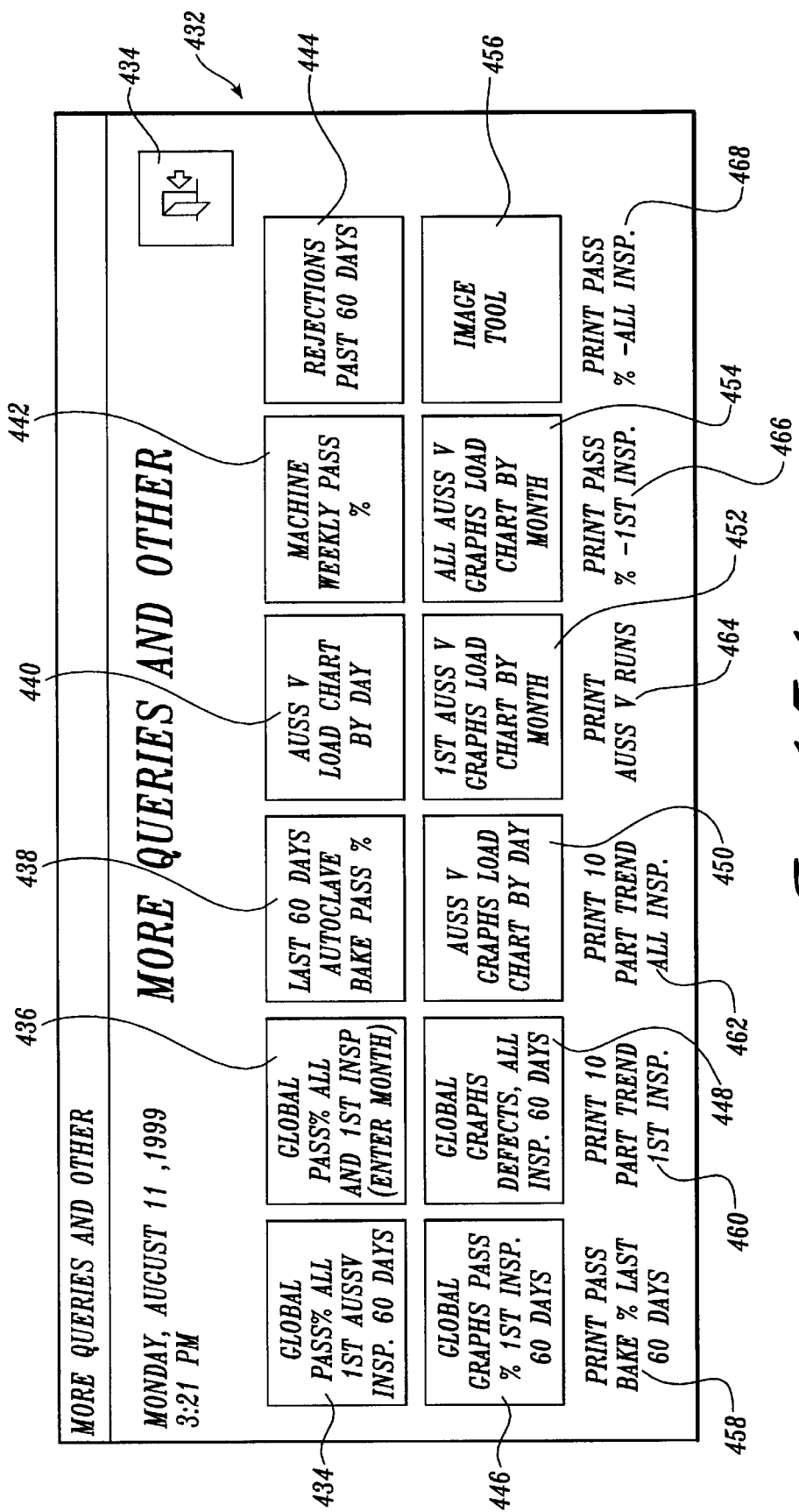
FIG. 15A is an exemplary MORE QUERIES and other window that is displayed when a button in the quality assurance DATA RECORD window is selected by a user.

FIG. 7 is a functional flow diagram that illustrates in detail the display composite part statistic and trend data step (block 118) of FIG. 2. Beginning at a start block, the logic moves to a block 142 when the QTS is selected by the user. As noted above, a QTS control center window that enables a user to select the QTS is shown in FIG. 8A and described below. Next, at a block 144, the user selects the QA DATA RECORD for the composite part to be displayed. At block 146, the QA DATA RECORD for the composite part is displayed. Stepping to a block 148, the user selects a historical trend graph of a composite part for display. Alternatively or thereafter, the logic flows to a block 150 where the user selects a historical statistic of the composite part for display. The historical trends and statistics displays are selected by actuating various window buttons that are illustrated in FIGS. 9A, 11A, and 15A and described below. Next, the logic returns to the main logic flow shown in FIG. 2 (end block).

As will be better understood from the following description, the graphs and historical statistics generated by a QTS formed in accordance with the invention can take on a variety of forms. The displays, which may take the forms of tables and graphs, may be based on user queries or may be based on regularly collated data. In one actual embodiment of the present invention, queries are identified by gray buttons, graphical reports are identified by maroon buttons, and other reports are identified by dark blue background buttons. This color-coding scheme is designed to help the users to determine the nature of the output that will occur when a button is selected. The buttons are used to control the displaying of inspection load charts, part inspection yields, and trends. All windows and reports in a search or a query are referenced to the time clock of the QTS server computer.

Figure 9B:
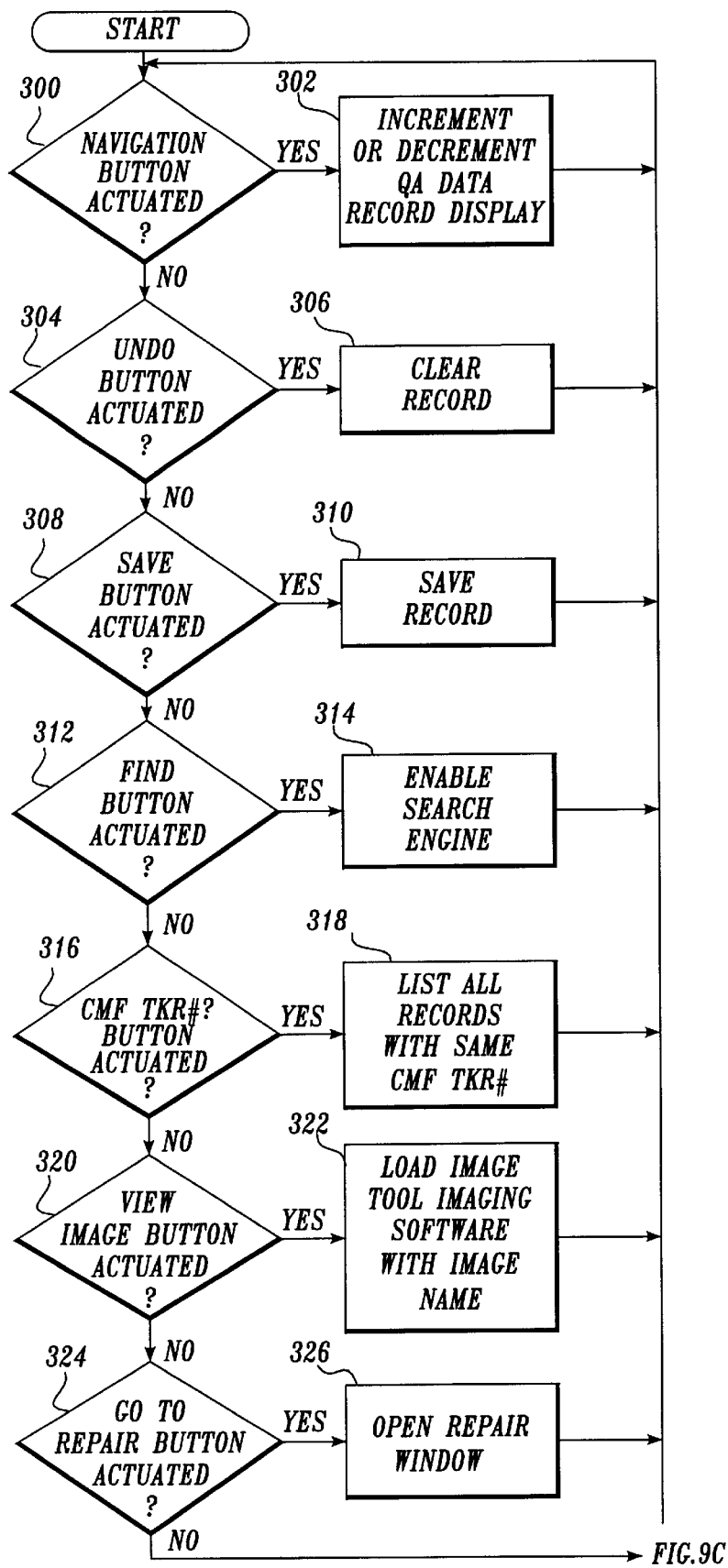
FIGS. 9B and 9C are a functional flow diagram for FIG. 9A.

When the QTS is activated by a user, a QTS control center window 160 automatically appears. A QTS control center window included in one actual embodiment of the invention is illustrated in FIG. 8A. The QTS control center window illustrated in FIG. 8A includes an Information Bulletin Board 162 that informs users of options, new items, future updates, time limits, etc. Preferably for data entry personnel, the Information Bulletin Board will display a user's name and inform the user of previous data entry errors or new features. General information in the form of graphs 164 may also be displayed. Further, preferably, the QTS includes on-line documentation that is accessed by pressing a button 166 labeled "QTS Documentation" in the QTS control center window. A button 168 labeled "Exit Quality Tracking System" in the QTS control center window closes the QTS. When a button 170 in the QTS control center window labeled BEGIN QTS is actuated, a QA DATA RECORD window automatically appears in a read-only mode. An example of a QA DATA RECORD window is illustrated in FIGS. 9A and 9B and described below. The QTS control center window 160 may also include the current date and time 172 and conventional window minimize, maximize, and close buttons 174.

Figure 8B:
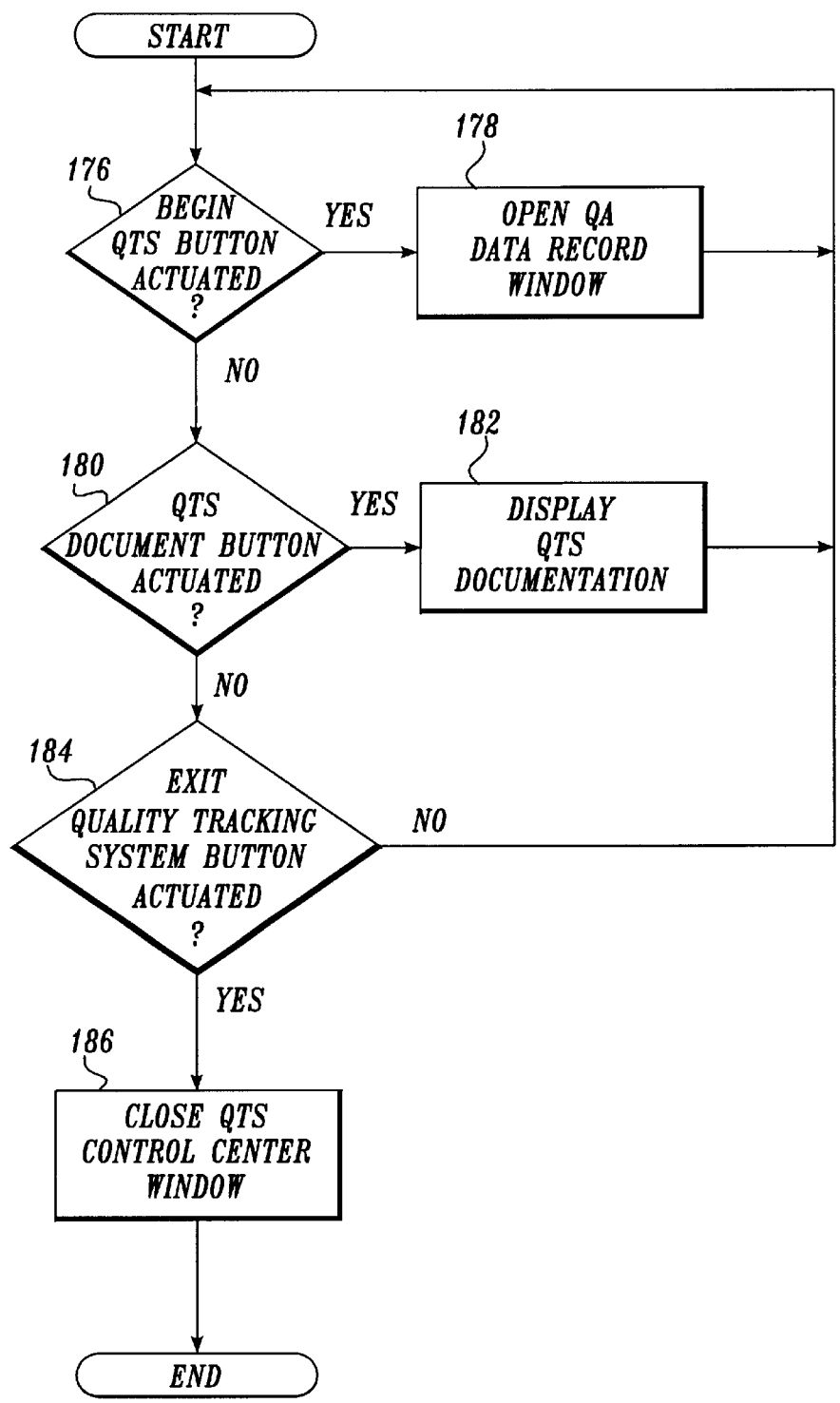
FIG. 8B is a functional flow diagram for FIG. 8A.

FIG. 8B is a functional flow diagram illustrating the operation of the QTS control center window shown in FIG. 8A. Stepping from a start block, a test 176 is made to determine if the Begin QTS button 170 has been activated. If the Begin QTS button has been activated, a QA DATA RECORD window 178 is opened. If the Begin QTS button 170 has not been activated, a test 180 is made to determine if the QTS Documentation button 166 has been activated. If the QTS Documentation button 166 has been activated, the first page of QTS documentation 182 is displayed. If the QTS Documentation button has not been activated, a test 184 is made to determine if the Exit Quality Tracking System button 168 has been actuated. If the Exit Quality Tracking System button 168 has been activated, the QTS control center window is closed 186 and the process ends. If the Exit Quality Tracking System button 168 is not activated or when the QA DATA RECORD window is closed or the QTS documentation display ends, the process cycles to the Begin QTS button actuated test 176.

Turning now to the QA DATA RECORD window (FIG. 9A), preferably, only personnel with permission may add process of inspection data to QA DATA RECORD. Further, preferably, when a QA DATA RECORD is added to the QTS, all input fields in the record must be completed before the record will be saved. QA DATA RECORD are the stepping stones to all other records, queries, and reports. Preferably, if a QA DATA RECORD is deactivated, all related records are disabled. All process of inspection data is referenced from the QA DATA RECORDS. In the embodiment of the invention being described herein the QA DATA RECORD is a one-page form that combines QA inspection data and AUSS V operating parameters.

The QA DATA RECORD window 188 illustrated in FIG. 9A includes a plurality of data entry boxes via which permitted personnel can enter data. Some of the boxes include drop down lists for ease of data entry. The illustrated data entry boxes include: a Machine Number box (drop down list) 190; a Part Number box 192; a Reference BAC box (drop down list) 194; a Requalification # box (drop down list) 196; a Scan Description 1 box 198; a Scan Description 2 box 200; an NCR # box 202; a Comments box 204; a Scan Date box 206; an LMF TRK # box 208; a New Tool ? box (drop down list-yes/no) 210; a Last Bake # box 212; a Tool Set # box (drop down list) 214; an Inspection # box (drop down list) 216; a Date File 1 box 218; a Date File 2 box 220; an Image Name 1 box 222; an Image Name 2 box 224; a Defect Attenuation box 226; a Defect Size box 28; a Defect Location box 230; and a # of Defects box (drop down list) 232. In the QA date record window 188 illustrated in FIG. 9A, only data related to the first scan of the identified part is available. Thus data is included only in the Scan Description 1 box 198, the Date File 1 box 218, and the Image Name 1 box 222. The Scan Description 2 box 200, the Date File 2 box 220 and the Image Name 2 box are denoted N/A (not available).

In addition to data boxes, the QA DATA RECORD shown in FIG. 9A may include fixed information, such as product family 234, Operator U # (entered automatically based on the identification of an operator entered at log on) 236; and a Log # (also entered automatically) 238, plus date information 240. The QA DATA RECORD window 188 also includes a Pass ? check box 242.

In addition to data entry boxes and other information, the QA DATA RECORD window includes a number of "buttons" that are used to navigate through QA DATA RECORDS and cause other windows and records to be displayed. A user of the QTS does not need to operate any of these buttons to complete a QA DATA RECORD and cause it to be stored.

At the far-left bottom of the QA DATA RECORD window are navigation control buttons 244. When clicked by a user, inner navigation control buttons 246 and 248 move up and down one record at a time. Outer navigation control buttons 250 and 252 move up or down a predetermined number of records. A center right arrow button 254 is used to start a new record. A number 256 to the right of the navigation buttons 244 is the total number of records. A number 258 inside of the navigation buttons is the position of the current record within the total number of records. The record number 258 is not necessarily the same as the Log # 238. The Log # 238 in the QA DATA RECORD window should match the Log # in the REPAIR RECORD window, illustrated in FIG. 11A and described below. The Log # is a real number that is used for tracking purposes. In contrast, the record number 258 in the navigation bar is relative to the number of records that are stored in the database. The record number does not include records that may have been archived and removed from the database; thus, neither the record number 258 or total number 256 have any relevant meaning.

Three control buttons 260, 262 and 264 located in the lower center of the QA DATA RECORD form are shown in FIG. 9A. The first control button 260, identified by an eraser icon (UNDO), clears the information that a user is entering data into the QA DATA RECORD window. The UNDO button does not remove updates to a previously entered QA DATA RECORD. The second control button 262 identified by a disc icon (SAVE) saves the QA DATA RECORD. Typically, only users such as QA personnel have permission to operate the SAVE button. The third control button 264 identified by a binocular icon (FIND) enables a search engine. All users may use the FIND button to launch searches for a composite part, e.g., a search for an NCR #, Bake #, TKR #, part number, or date.

A small button with a question mark 266 located near the CMF TKR # field of the QA DATA RECORD provides a quick query listing for all records with same CMF TKR #. This quick query button may be used by AUSS V operators and others to review previous entries in the database. FIG. 10 is an exemplary illustration of a quick query listing display that occurs when the small button with a question mark 266 is activated.

Two control buttons 268 and 270 located in the middle right of the QA DATA RECORD are labeled VIEW IMAGE. Each button references an image name that is listed in the Image Name data box 222 or 224 located to the left of the button. When either button is selected, imaging software is loaded and the listed image is displayed.

Two control buttons 272 and 274 labeled GO TO REPAIR and MORE QUERIES are located above an analysis row of buttons. When actuated, the GO TO REPAIR button 272 launches a REPAIR RECORD window shown in FIG. 11A and described below. When activated, the MORE QUERIES button 274 launches a MORE QUERIES window shown in FIG. 15A and described below. Also, various fields in the REPAIR RECORD, part numbers, and part image may be directly referenced from the QA DATA RECORD form.

Six analysis buttons 276, 278, 280, 282, 284 and 286, located in the bottom of the QA DATA RECORD form, when actuated, cause various displays to occur. The left four buttons titled PART TREND 1st INSP., PASS % 1st INSP <60 DAYS, PASS % TOTAL <60 DAYS, and AUSS V RUN cause reports of the type illustrated in FIGS. 21, 22, and 23 and described below to be displayed. The last two buttons on the right titled TREND GRAPHS 1st INSP. and TREND GRAPHS 1st INSP. (MONTHLY) cause trend graphs of the type illustrated in FIGS. 12 and 13 and described below to be displayed.

Figure 9C:
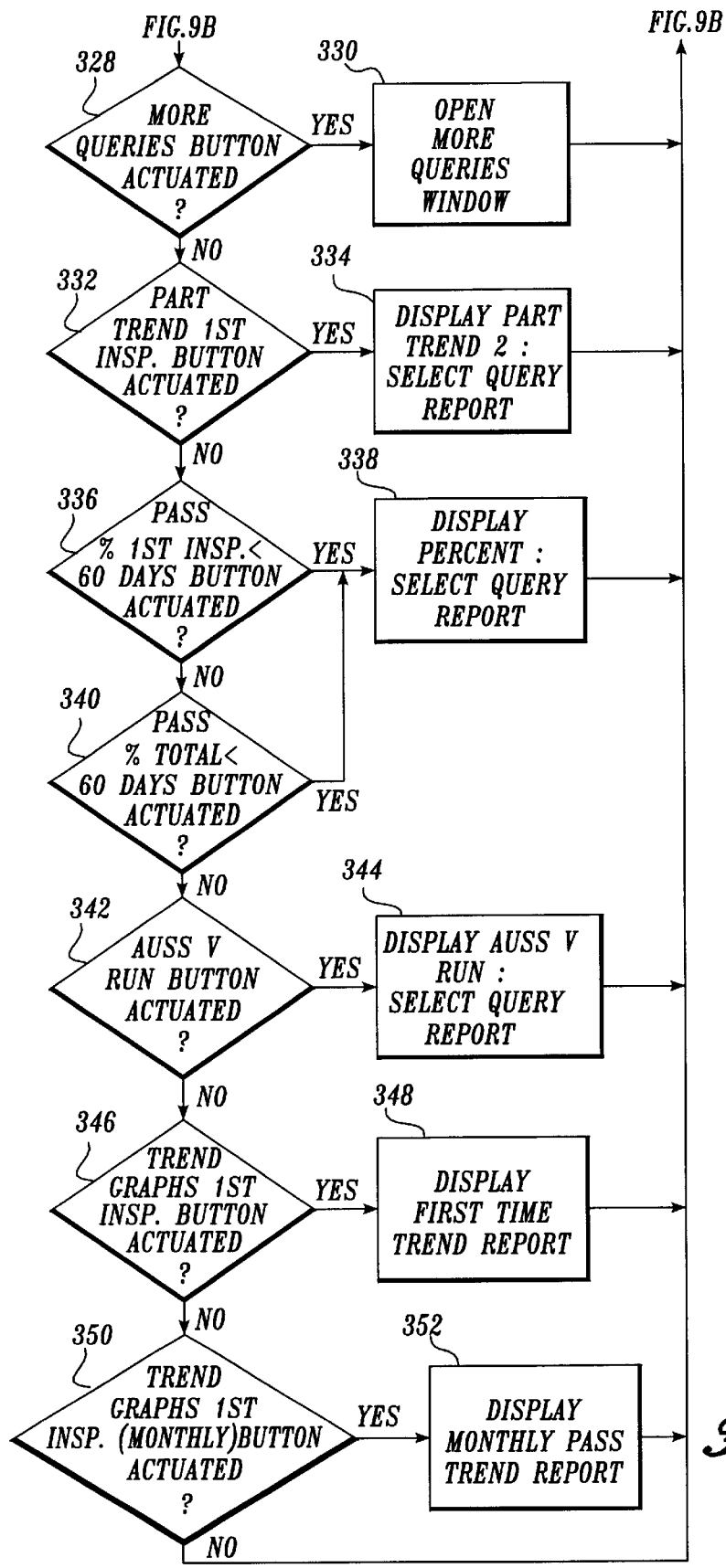

FIGS. 9B and 9C are a functional flow diagram illustrating the operation of the various control buttons included in the QA DATA RECORD window shown in FIG. 9A and described above. After a start block, as shown in FIG. 9B, a test 300 is made to determine if one of the navigation buttons 244 have been actuated. If one of the navigation buttons have been actuated, the QA DATA RECORD display is incremented or decremented, as appropriate. See block 302. Then the process cycles to the navigation button activated test 300. If none of the navigation buttons have been actuated, a test 304 is made to determine if the UNDO button 260 has been actuated. If the UNDO button 260 has been actuated, the data in the QA DATA RECORD boxes is cleared. See block 306. Then the process cycles to the navigation button test 300.

If the UNDO button 260 has not been actuated, a test 308 is made to determine if the SAVE button 262 has been actuated. If the SAVE button has been actuated, the current QA DATA RECORD information is stored, provided the entered data is complete. See block 310. Then the process cycles to the navigation button test 300. If the SAVE button 262 has not been actuated, a test 312 is made to determine if the FIND button 264 has been actuated. If the FIND button has been actuated, a search engine is enabled. See block 314. When the search is complete and the search engine is closed, the process cycles to the navigation button actuated test 300.

If the FIND button 264 has not been actuated, a test 316 is made to determine if the CMF TKR # ? button has been actuated. If the CMF TKR # ? button has been actuated, all records with the same CMF TKR number are listed. See block 318. When the display listing all records with the same CMF TKR number is closed, the process cycles to the navigation button actuated test 300.

If the CMF TKR # ? button is not actuated, a test 320 is made to determine if one of the VIEW IMAGE buttons 268 or 270 has been actuated. If one of the VIEW IMAGE buttons has been actuated, image tool imaging software is loaded with the image name and the appropriate image displayed. While various imaging software can be utilized, one suitable software for images in a TIFF format is Image Tool Version 1.27 available from UTHSCSA (University of Texas Health Science Center, San Antonio, Tex.). When the image display is closed, the process cycles to the navigation button actuated test 300. If neither of the VIEW IMAGE buttons 268 or 270 have been actuated, a test 324 is made to determine if the GO TO REPAIR button 272 has been actuated. If the GO TO REPAIR button has been actuated, the repair window illustrated in FIG. 11 and described below is opened. See block 326. When the repair window is closed, the process cycles to the navigation button actuated test 300.

If the GO TO REPAIR button has not been actuated, a test 328 (FIG. 9C) is made to determine if the MORE QUERIES button 274 has been actuated. If the MORE QUERIES button has been actuated, the MORE QUERIES window illustrated in FIG. 15A and described below is opened. See block 330. When the MORE QUERIES window is closed, the process cycles to the navigation button actuated test 300.

If the MORE QUERIES button has not been actuated, a test 332 is made to determine if the PART TREND 1st INSP. button 276 has been actuated. If the PART TREND 1st INSP. button 276 has been actuated, a display titled PART TREND 2: SELECT QUERY report is displayed. See block 334. An exemplary PART TREND 2: SELECT QUERY display is illustrated in FIG. 21 and described below. When the PART TREND 2: SELECT QUERY report display is closed, the process cycles to the navigation button actuated test 300.

If the PART TREND 1st INSP. button has not been actuated, a test 336 is made to determine if the PAST % 1st INSP. <60 DAYS button 278 has been actuated. If the PAST % 1st INSP. <60 DAYS button has been actuated, a display titled PERCENT: SELECT QUERY report is displayed. See block 338. An exemplary PERCENT: SELECT QUERY report display is illustrated in FIG. 22 and described below. When the PERCENT: SELECT QUERY report display is closed, the process cycles to the navigation button actuated test 300. If the PAST % 1st INSP. <60 DAYS button has not been actuated, a test 340 is made to determine if the PAST % TOTAL <60 DAYS button 280 has been actuated. If the PAST % TOTAL <60 DAYS button is actuated, the PERCENT: SELECT QUERY report (block 338) is displayed.

If the PAST % TOTAL <60 DAYS button 280 has not been actuated, a test 342 is made to determine if the AUSS V RUN button 282 is actuated. If the AUSS V RUN button is actuated, a display titled AUSS V RUN: SELECT QUERY report is displayed. See block 344. When the AUSS V RUN: SELECT QUERY report display is closed, the process cycles to the navigation button activated test 300.

Figure 12:
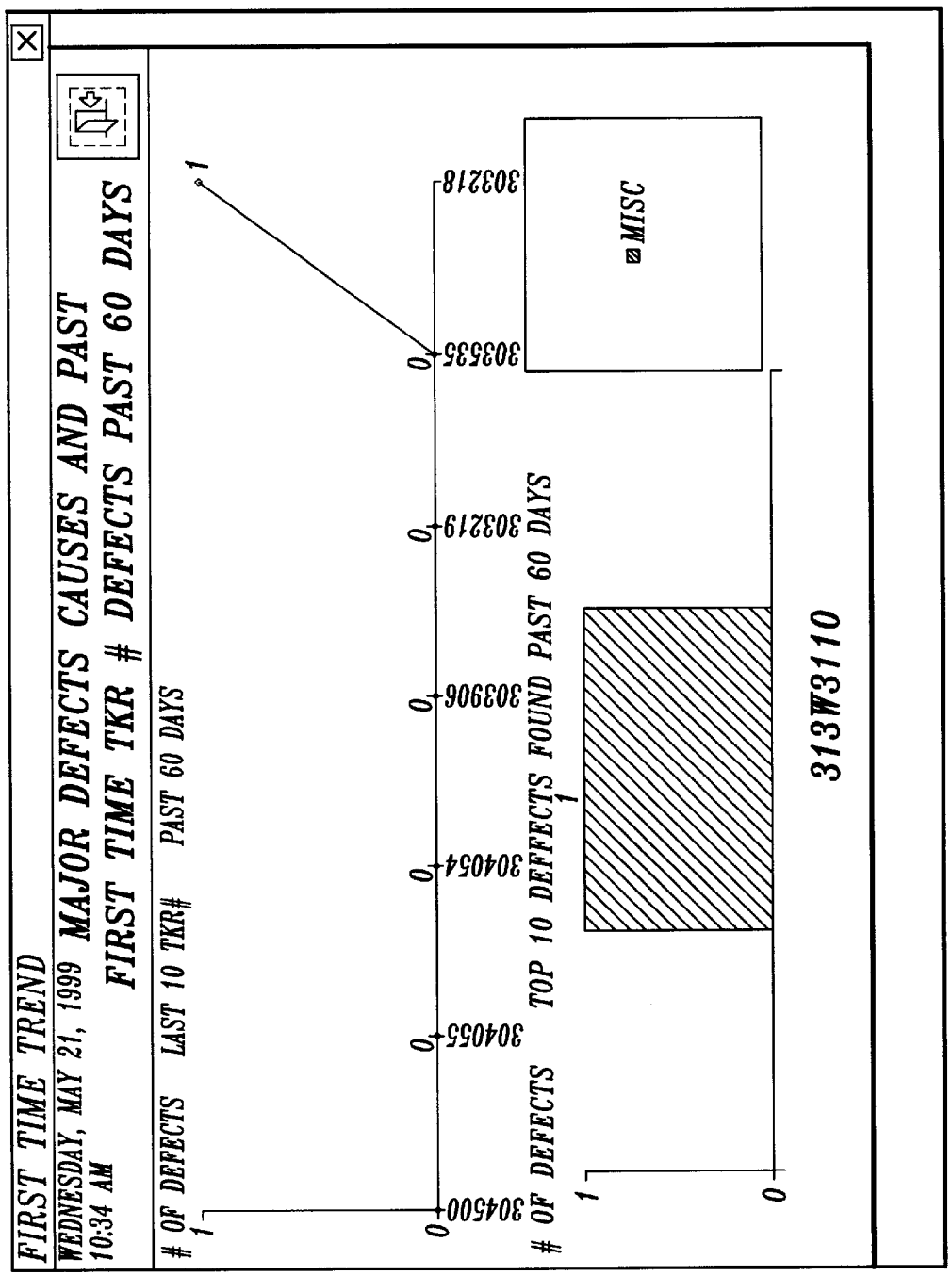
FIG. 12 is an exemplary first time trend report that is displayed when a button in the quality assurance DATA RECORD window is selected by a user.

If the AUSS V RUN button has not been actuated, a test 346 is made to determine if the TREND GRAPHS 1st INSP. button 284 has been actuated. If the TREND GRAPHS 1st INSP. button has been actuated, a First Time Trend report is displayed. See block 348. An example of a FIRST TIME TREND report is illustrated in FIG. 12 and described below.

When the FIRST TIME TREND report display is closed, the process cycles to the navigation button actuated test 300.

Figure 13:
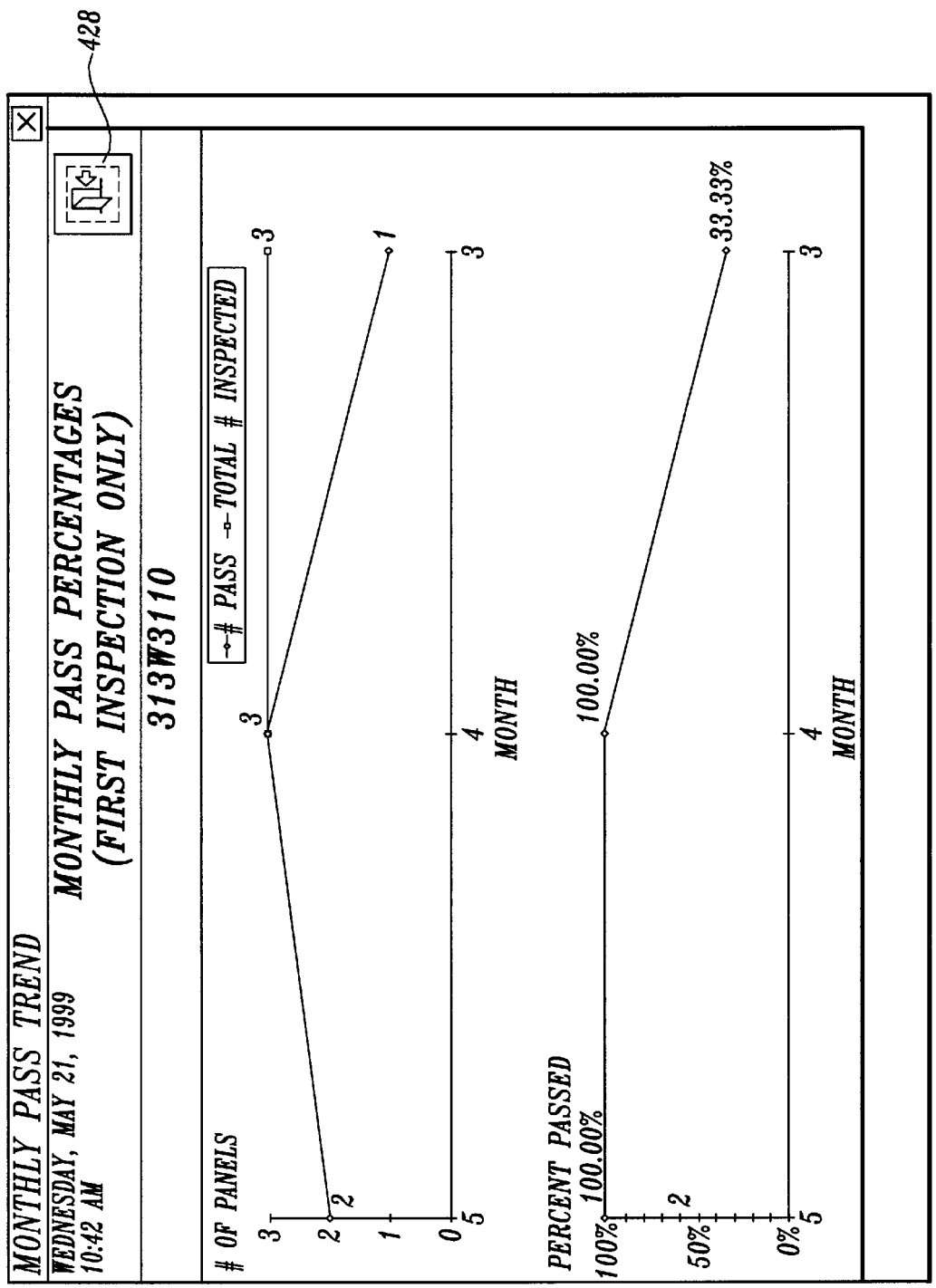
FIG. 13 is an exemplary monthly pass trend report that is displayed when a button in the quality assurance DATA RECORD window is selected by a user.

If the TREND GRAPHS 1st INSP. button 284 has not been actuated, a test 350 is made to determine if the TREND GRAPHS 1st INSP. (MONTHLY) button 286 has been actuated. If the TREND GRAPHS 1st INSP. (MONTHLY) button has been actuated, a MONTHLY PASS TREND report is displayed. See block 352. An example of a MONTHLY PASS TREND report is illustrated in FIG. 13 and described below. When the MONTHLY PASS TREND report display is closed, the process cycles to the navigation button activated test 300. Likewise, if the TREND GRAPHS 1st INSP. (MONTHLY) button has not been actuated, the process cycles to the navigation button actuated test 300.

Data entered into the REPAIR RECORD window 358 illustrated in FIG. 11A and described next is saved with data entered in the QA DATA RECORD. The two windows are related by a common log number. They do not have common fields. The log number 360 of the exemplary REPAIR RECORD shown in FIG. 11A is located to the right of a button 362 with a floppy disk icon (SAVE). Preferably the log number cannot be edited. Likewise, preferably, the log number 238 of the QA DATA RECORD window cannot be edited. It is important to note that when the log numbers in both windows are not the same, the database is in need of repair. Also, preferably the REPAIR RECORD window opens in a read-only mode when called from the QA DATA RECORD form. Only personnel with write permission may modify the data in the REPAIR RECORD form. Like the QA DATA RECORD window, the REPAIR RECORD window 358 includes a plurality of data entry boxes, some of which include drop-down lists. The data entry boxes of the exemplary REPAIR RECORD window 358 illustrated in FIG. 9A include a Repair Date box 364; a Repair Operator box 366; a Defect Type Found box (drop down list) 368; a TKR # box 370; a Repair NCR # box 372; a Defect Location box (drop down list) 374; a Repair Comments box 376; and an Other Defects box 378. In addition to data entry boxes, the REPAIR RECORD window 358 may include other information, such as the current date 380 and standard view image titles 382, 384 such as Standard Image 1 315W1527-80L and Standard Image 2 315W1527-80R shown in the exemplary REPAIR RECORD window 358 shown in FIG. 11A.

In addition to entered and automatically generated information, the REPAIR RECORD window 358 includes a plurality of control buttons. Located in the upper-right corner of the REPAIR RECORD window is an exit button 386 that, when actuated, closes the REPAIR RECORD window. (All windows and displays other than the QA DATA RECORD window include a similar exit button. In order to avoid unnecessary duplication of description, such exit buttons are not further described in detail.)

Located beneath the Standard Image 1 315W1527-80L and Standard Image 2 315W1527-80R descriptions are two control buttons 388 and 390 titled EDIT/VIEW IMAGE, one associated with each description. When either of two EDIT/VIEW IMAGE buttons are actuated, a bitmap image viewer, such as the Microsoft Paint Win 95 Version 4.00.950 Standard Image View, is launched and the identified image displayed. The viewer will only function properly if a file is saved with the default name contained in the description positioned directly above the selected button. The image displayed by the bitmap image viewer may be annotated with other (i.e., repair) information.

When actuated, a control button 392 titled CAMERA IMAGE OF CORE launches a photo editor that displays a digital picture of a repaired core for the composite part. The photo editor may contain up to four files loaded under the file menu of the photo editor. A suitable photo editor program is Microsoft Photo Editor Version 96101200.

Figure 14:
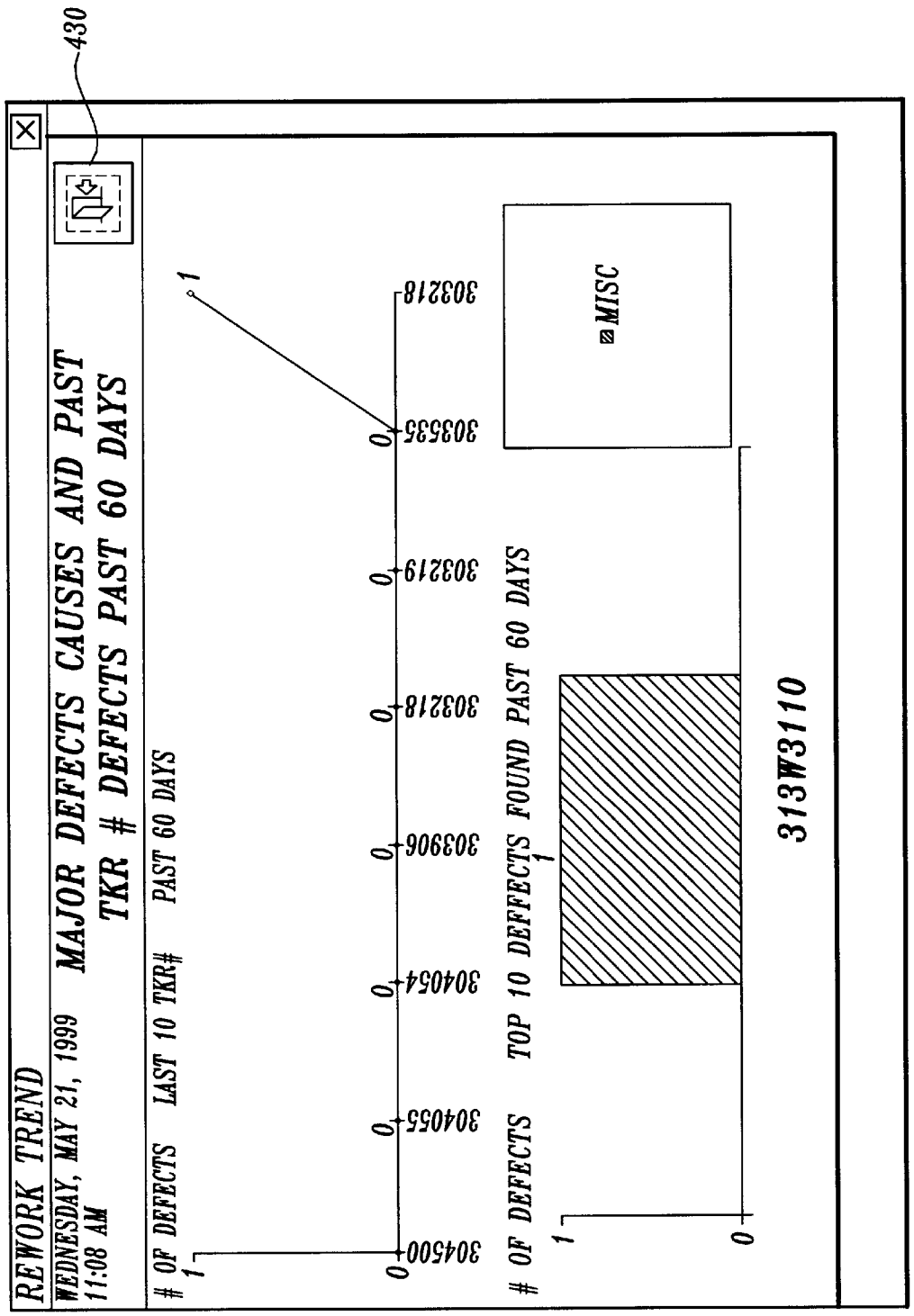
FIG. 14 is a rework trend report that is displayed when a button in the REPAIR RECORD window is selected by a user.

A three-button 394, 396 and 398 group is located on the bottom right side of the REPAIR RECORD window. The left-most button 394, labeled PART TREND (ALL INSP.), causes a 10-part trend analysis display that includes all re-inspections to occur. This display titled PART TREND: SELECT QUERY is substantially similar to a similarly identified button in the QA DATA RECORD window and is described below. An example of a PART TREND: SELECT QUERY display is shown in FIG. 24 and described below. When the middle button 396 labeled TREND GRAPHS (ALL INSP.) is actuated, a Rework Trend display occurs. An example of a Rework Trend display is illustrated in FIG. 14 and described below. When actuated, the right side button 398 labeled SELECT IMAGE opens a window (not shown) that allows an operator to type in any image name listed in the records and view the image.

Figure 11B:
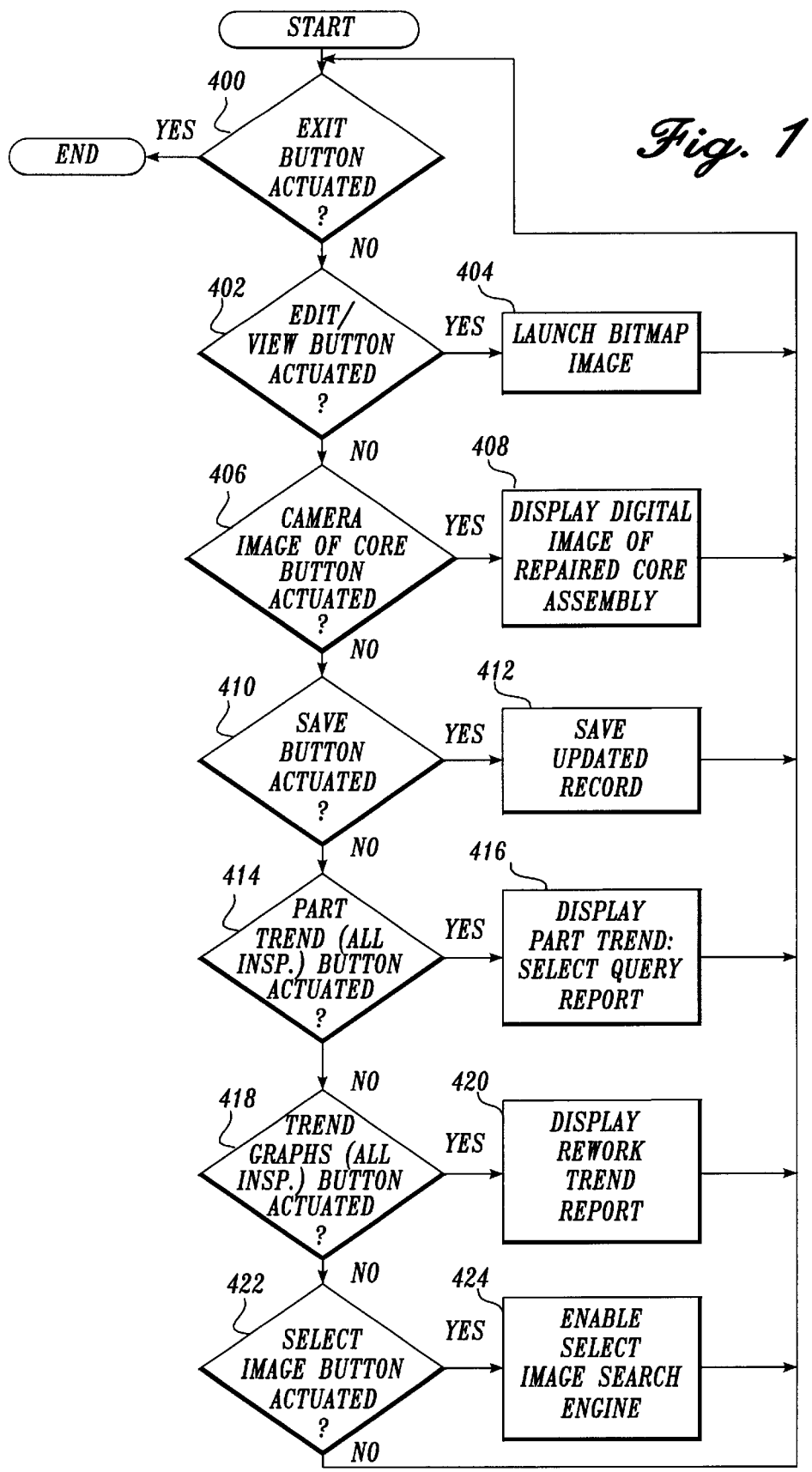
FIG. 11B is a functional flow diagram for FIG. 11A.

FIG. 11B is a functional flow diagram illustrating the operation of the REPAIR RECORD window illustrated in FIG. 11A and described above. After the REPAIR RECORD window is opened, the process shifts from a start block to a test 400 to determine if the exit button has been actuated. If the exit button 386 has been actuated, the process ends and the program cycles to the QA DATA RECORD window illustrated in FIG. 9A and described above. If the exit button has not been actuated, a test 402 is made to determine if one of the EXIT/VIEW IMAGE buttons 388 or 390 has been actuated. If one of the EXIT/VIEW IMAGE buttons has been actuated, the bitmap image viewer is launched, as described above. See block 404. When the bitmap image viewer is closed, the process cycles to the exit button actuated test 400.

If neither of the EXIT/VIEW IMAGE buttons 388 or 390 have been actuated, a test 406 is made to determine if the CAMERA IMAGE OF CORE button 390 has been actuated. If the CAMERA IMAGE OF CORE button has been actuated, the photo editor program is launched and a digital image of the repaired core assembly is displayed. See block 408. When the photo editor program is closed, the process cycles to the exit button actuated test 400.

If the CAMERA IMAGE OF CORE button 392 has not been actuated, a test 410 is made to determine if the SAVE button 362 has been actuated. If the SAVE button has been actuated, the updated record is saved. See block 412. After the updated record is saved, the process cycles to the exit button actuated test 400.

If the SAVE button 362 has not been actuated, a test 414 is made to determine if the PART TREND (ALL INSP.) button 394 has been actuated. If the PART TREND (ALL INSP.) button has been actuated, a PART TREND: SELECT QUERY report is displayed. An example of a PART TREND: SELECT QUERY report is illustrated in FIG. 24 and described below. When the PART TREND: SELECT QUERY report display is closed, the process cycles to the exit button actuated test 400.

If the PART TREND (ALL INSP.) button 394 has not been actuated, a test 418 is made to determine if the TREND GRAPHS (ALL INSP.) button 396 has been actuated. If the TREND GRAPHS (ALL INSP.) button has been actuated, a rework trend report is displayed. See block 420. An example of a rework trend report is illustrated in FIG. 14 and described below. When the rework trend report display is closed, the process cycles to the exit button actuated test 400. If the TREND GRAPHS (ALL INSP.) button 396 has not been actuated, a test 422 is made to determine if the SELECT IMAGE button 398 has been actuated. If the SELECT IMAGE button 398 has been actuated, a SELECT IMAGE window is opened. See block 424. When the SELECT IMAGE window is closed or if the SELECT IMAGE button 398 has not been actuated, the process cycles to the exit button actuated test 400.

An example of a first time trend report is illustrated in FIG. 12. This report is displayed when the TREND GRAPHS 1st INSP. button 284 in the QA DATA RECORD window 188 (FIG. 9A) is actuated. An exit button 426 is located at the top-right corner of the FIRST TIME TREND report. When actuated, the exit button 426 closes the FIRST TIME TREND report. The FIRST TIME TREND report provides a graphical view of a 10-part trend (or less if 10 parts have not been manufactured) and defects found in the past 60 days. The latest TKR # (Part Serial #) is located on the left side in the top graph and the tenth (or less if less than 10 parts have been manufactured) TKR # inspected is located on the right side.

An example of a MONTHLY PASS TREND report is shown in FIG. 13. This report is displayed when the TREND GRAPHS 1st INSP. (MONTHLY) button 286 in the QA DATA RECORD window 188 (FIG. 9A) is actuated. An exit button 428 is located at the top-right corner of the MONTHLY PASS TREND report. The MONTHLY PASS TREND report displays a graphical view of the past month's inspection pass percentages for the composite part identified in the part number box 194 of the QA DATA RECORD window 188. Two graphs are included, one showing the number of parts (panels) produced during the months shown in the report, and the other showing the number of parts that passed inspection. The current month is listed on the left of both charts in the MONTHLY PASS TREND report. At the far right side of the report is located the beginning month stored in the database. Preferably, the graphs are for the current year.

An example of a REWORK TREND report is shown in FIG. 14. This report is displayed when the TREND GRAPHS (ALL RUNS) button 396 in the REPAIR RECORD window 358 (FIG. 11A) is actuated. An exit button 430 is positioned at the top-right corner of the REWORK TREND report. This report includes a graphical view of the 10-part trend (including all reruns) and defects found in the past 60 days for the composite part, or less than 10 if less than 10 parts have been manufactured. The latest TKR # is disposed on the left of the top graph and the tenth (or less) TKR # inspected is found on the right of the REWORK TREND report. Information older than 60 days is accessed using buttons displayed in the QA DATA RECORD window and described below.

A MORE QUERIES and other window 432 is illustrated in FIG. 15A. This window is displayed when the MORE QUERIES button 274 in the QA DATA RECORD 188 (FIG. 9A) is actuated. The MORE QUERIES and other window 432 includes three rows of control buttons and an exit button 434. In general, the top row buttons relate to queries, the middle row buttons relate to reports, and the bottom row buttons relate to printouts. A button labeled IMAGE TOOL located at the end of the middle row launches an image viewer. The exit button 434 is positioned in the top right corner of the MORE QUERIES and other window.

The first row of the MORE QUERIES and other window 432 includes six buttons 434, 436, 438, 440, and 442 titled, respectively: GLOBAL PASS % ALL 1st AUSS V INSP. 60 DAYS, GLOBAL PASS % ALL AND 1st INSP. (ENTER MONTH), LAST 60 DAYS AUTOCLAVE BAKE PASS %, AUSS V LOAD CHART BY DAY, MACHINE WEEKLY PASS %, and REJECTIONS PAST 60 DAYS. When any of these buttons are actuated, a suitable query is generated and a response to the query is displayed. Examples of the displays that occur when any of these buttons are actuated are illustrated in FIGS. 25–32 and described below.

The second row buttons of the MORE QUERIES and other window 432 also includes six buttons 446, 448, 450, 452, 454, and 456 titled, respectively: GLOBAL PASS % 1st INSP. 60 DAYS; GLOBAL GRAPHS DEFECTS, ALL INSP. 60 DAYS; AUSS V GRAPHS LOAD CHART BY DAY; 1st AUSS V GRAPHS LOAD CHART BY MONTH; ALL AUSS V GRAPHS LOAD CHART BY MONTH; and IMAGE TOOL. As with the first row of buttons, except for the last button, when any of the buttons of the second row are actuated, a suitable report is displayed. Examples of such reports are illustrated in FIGS. 16–20 and described below.

The last row of the MORE QUERIES and other window 432 also includes six buttons 458, 460, 462, 464, 466 and 468 titled, respectively: PRINT PASS BAKE % LAST 60 DAYS, PRINT 10 PART TREND 1st INSP., PRINT 10 PART TREND ALL INSP., PRINT AUSS V RUNS, PRINT PASS %–1st INSP., and PRINT PASS % ALL INSP. When any of the last row of buttons is actuated, the designated report is printed out on a printer attached to the QTS.

Figure 15B:
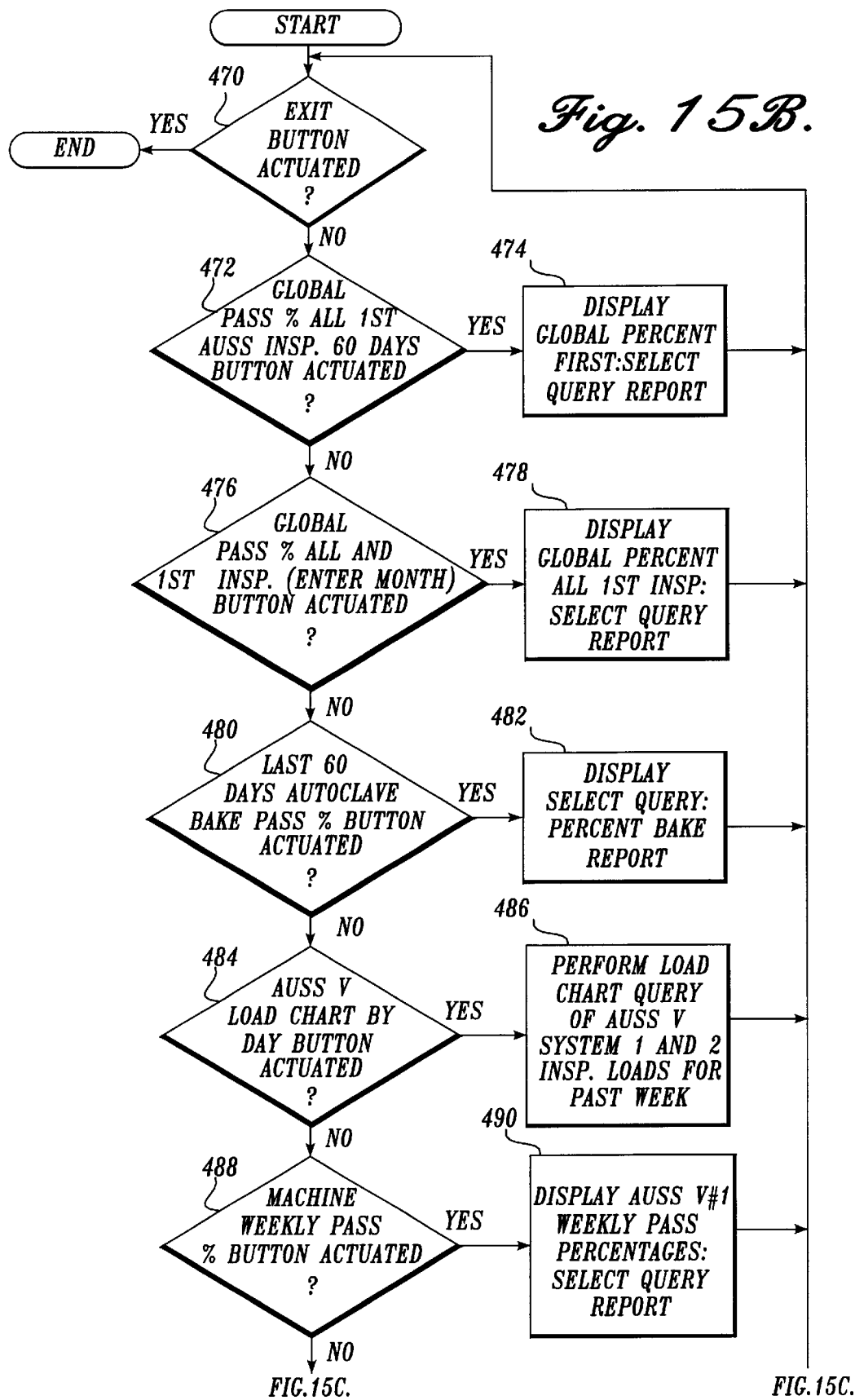
Figure 15D:
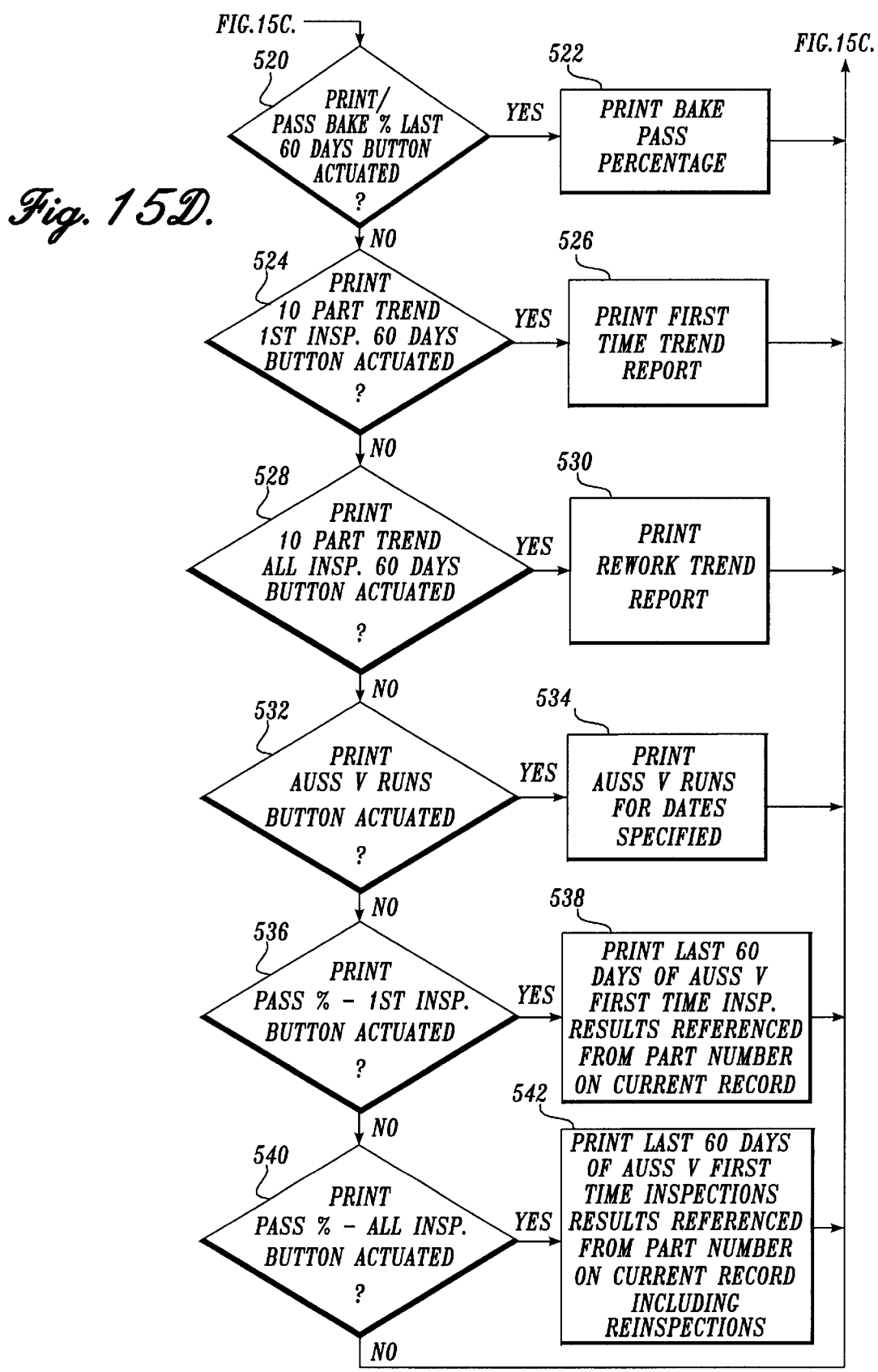

FIGS. 15B, 15C, and 15D are a functional flow diagram illustrating the operation of the MORE QUERIES and other window 432 illustrated in FIG. 15A. After a start block, as shown in FIG. 15B, the process begins with a test 470 to determine if the exit button 434 has been actuated. If the exit button has been actuated, the process ends and the MORE QUERIES and other window 432 closes. If the exit button has not been actuated, a test 472 is made to determine if the GLOBAL PASS % ALL 1st AUSS V INSP. 60 DAYS button 434 has been actuated. If the GLOBAL PASS % ALL 1st AUSS V INSP. 60 DAYS button has been actuated, a GLOBAL % FIRST: SELECT QUERY report, an example of which is illustrated in FIG. 25 and described below, is displayed. See block 434. When the GLOBAL % FIRST: SELECT QUERY report is closed, the process cycles to the exit button actuated test 470.

If the GLOBAL PASS % ALL 1st AUSS V INSP. 60 DAYS button has not been actuated, a test 476 is made to determine if the GLOBAL PASS % ALL AND 1st INSP. (ENTER MONTH) button 436 has been actuated. If the GLOBAL PASS % ALL AND 1st INSP. (ENTER MONTH) button has been actuated, a GLOBAL % ALL 1ST INSP.: SELECT QUERY reports, examples of which are illustrated in FIGS. 26–29 and described below, are sequentially displayed. When the GLOBAL % ALL 1ST INSP: SELECT QUERY reports are closed, the process cycles to the exit button actuated test 470.

If the GLOBAL PASS % ALL AND 1st INSP. (ENTER MONTH) button has not been actuated, a test 480 is made to determine if the LAST 60 DAYS AUTOCLAVE BAKE PASS % button 438 has been actuated. If the LAST 60 DAYS AUTOCLAVE BAKE PASS % button has been actuated, a SELECT QUERY: PERCENT BAKE report is displayed. See block 482. An example of a SELECT QUERY: PERCENT BAKE report is illustrated in FIG. 30 and described below. When the SELECT QUERY: report display is closed, the process cycles to the exit button actuated test 470.

If the LAST 60 DAYS AUTOCLAVE BAKE PASS % button has not been actuated, a test 484 is made to determine if the AUSS V LOAD CHART BY DAY button 440 has been actuated. If the AUSS V LOAD CHART BY DAY button has been actuated, a Load Chart Query of AUSS V SYSTEM 1 and 2 INSPECTION LOADS FOR THE LAST WEEK is performed. Thereafter, the process cycles to the exit button actuated test 470.

If the AUSS V LOAD CHART BY DAY button has not been actuated, a test 488 is made to determine if the MACHINE WEEKLY PASS % button has been actuated. If the MACHINE WEEKLY PASS % button is actuated, a AUSS V#1 WEEKLY PASS PERCENTAGES: SELECT QUERY report is displayed. See block 490. An example of a AUSS V WEEKLY PASS PERCENTAGES SELECT QUERY report is illustrated in FIG. 31 and described below. After the AUSS V #1 WEEKLY PASS PERCENTAGES: SELECT QUERY report is closed, the process cycles to the exit button actuated test 470.

If the MACHINE WEEKLY PASS % button 442 has not been actuated, a test 492 (FIG. 15C) is made to determine if the REJECTIONS PAST 60 DAYS button 444 has been actuated. If the REJECTIONS PAST 60 DAYS button has been actuated, a REJECTIONS PAST 60 DAYS SELECT QUERY report is displayed. See block 494. An example of a REJECTIONS PAST 60 DAYS: SELECT QUERY report is illustrated in FIG. 32 and described below.

Figure 16:
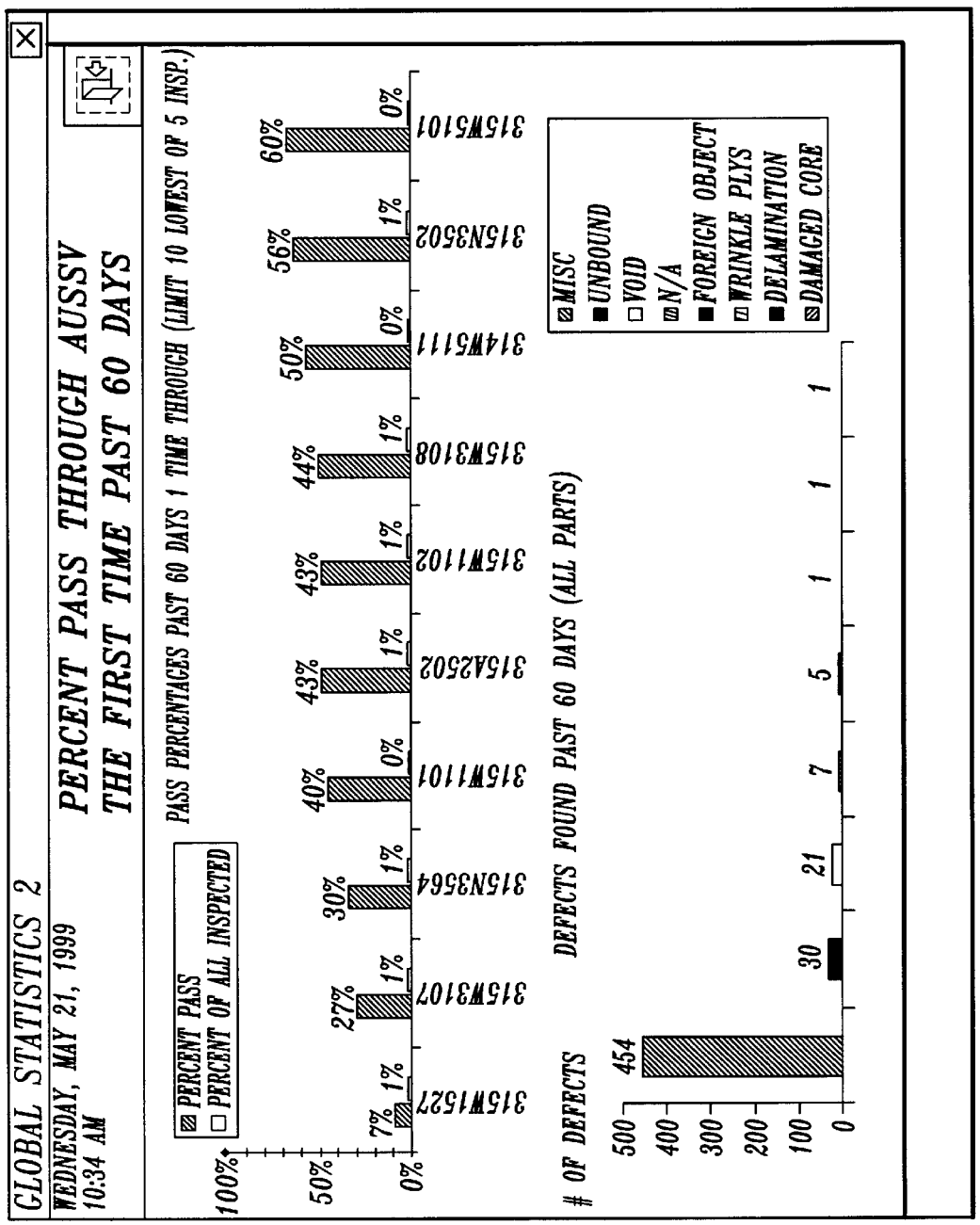
FIG. 16 is an exemplary global statistics 2 report that is displayed when a button in the MORE QUERIES and other window is selected by a user.

If the REJECTIONS PAST 60 DAYS button has not been actuated, a test 496 is made to determine if the GLOBAL GRAPHS PASS % 1st INSP. 60 DAYS button 446 has been actuated. If the GLOBAL GRAPHS PASS % 1st INSP. 60 DAYS button has been actuated, a GLOBAL STATISTICS 2 report is displayed. See block 498. An example of a GLOBAL STATISTICS 2 report is illustrated in FIG. 16 and described below.

Figure 17:
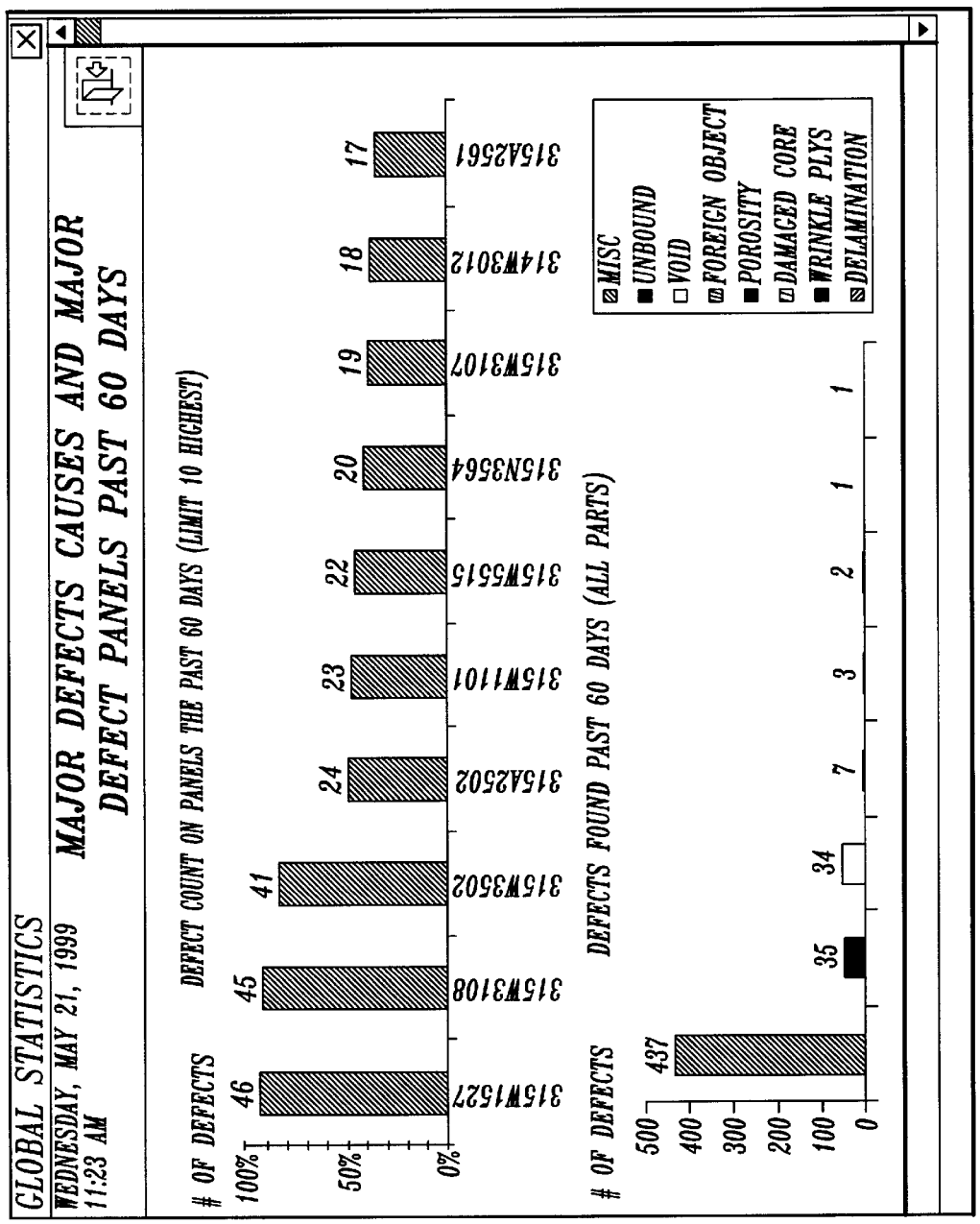
FIG. 17 is an exemplary global statistics report that is displayed when a button in the MORE QUERIES and other window is selected by a user.

If the GLOBAL GRAPHS PASS % 1st INSP. 60 DAYS button 446 has not been actuated, the test 500 is made to determine if the GLOBAL GRAPHS DEFECTS ALL INSP. 60 DAYS button 448 has been actuated. If the GLOBAL GRAPHS DEFECTS ALL INSP. 60 DAYS button has been actuated, a GLOBAL STATISTICS report is displayed. See block 502. An example of a GLOBAL STATISTICS report is illustrated in FIG. 17 and is described below. When the GLOBAL STATISTICS report is closed, the process cycles to the exit button actuated test 470.

Figure 18:
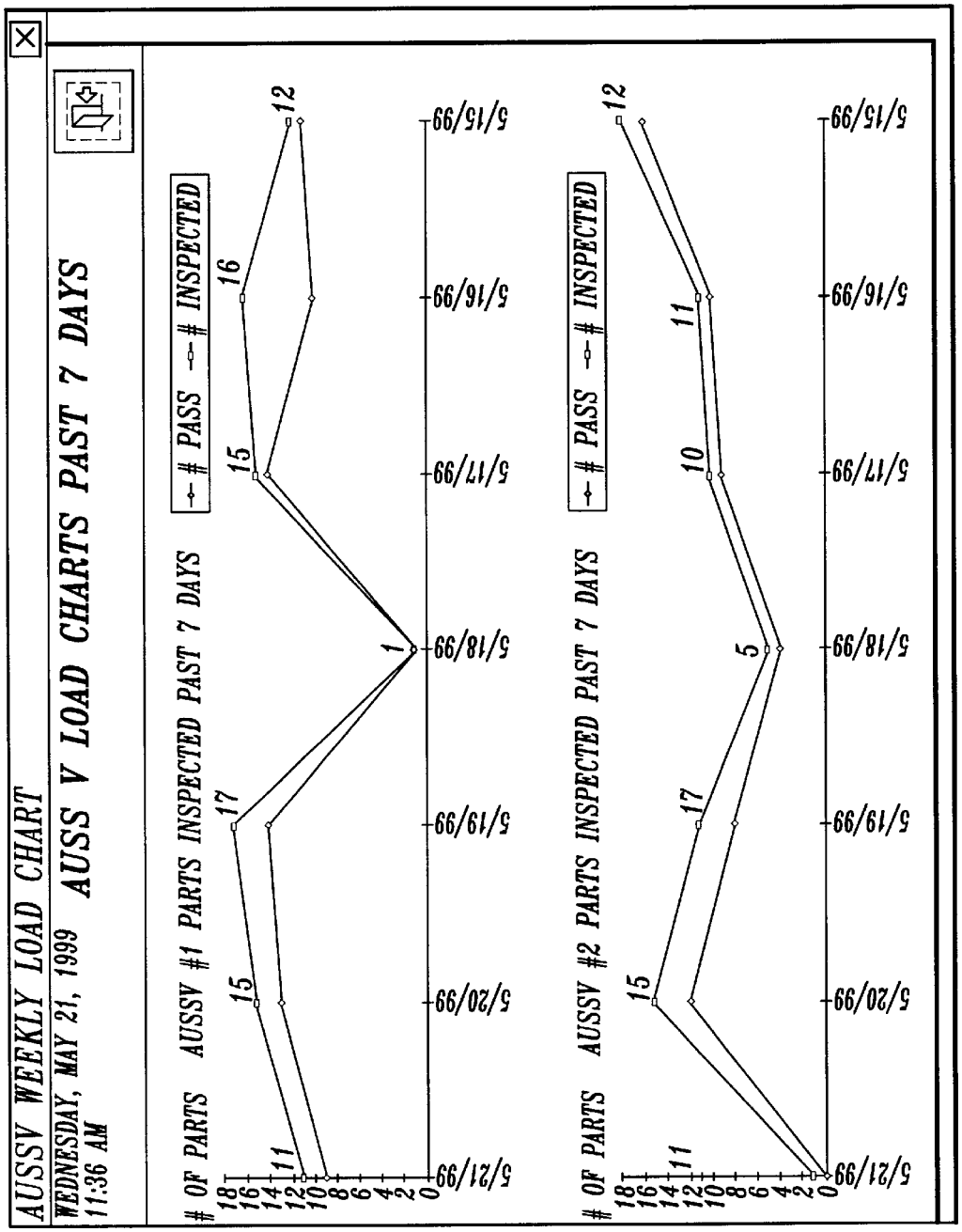
FIG. 18 is an exemplary advanced automated ultrasonic scanning system version five (AUSS V) weekly load chart report that is displayed when a button in the MORE QUERIES and other window is selected by a user.

If the GLOBAL GRAPHS DEFECTS ALL DAYS INSP. 60 DAYS button has not been actuated, a test 504 is made to determine if AUSS V GRAPHS LOAD CHARTS BY DAY button 450 has been actuated. If the AUSS V GRAPHS LOAD CHARTS BY DAY button has been actuated, an AUSS V WEEKLY LOAD CHART report is displayed. See block 506. An example of an AUSS V WEEKLY LOAD report is illustrated in FIG. 18 and described below.

Figure 19:
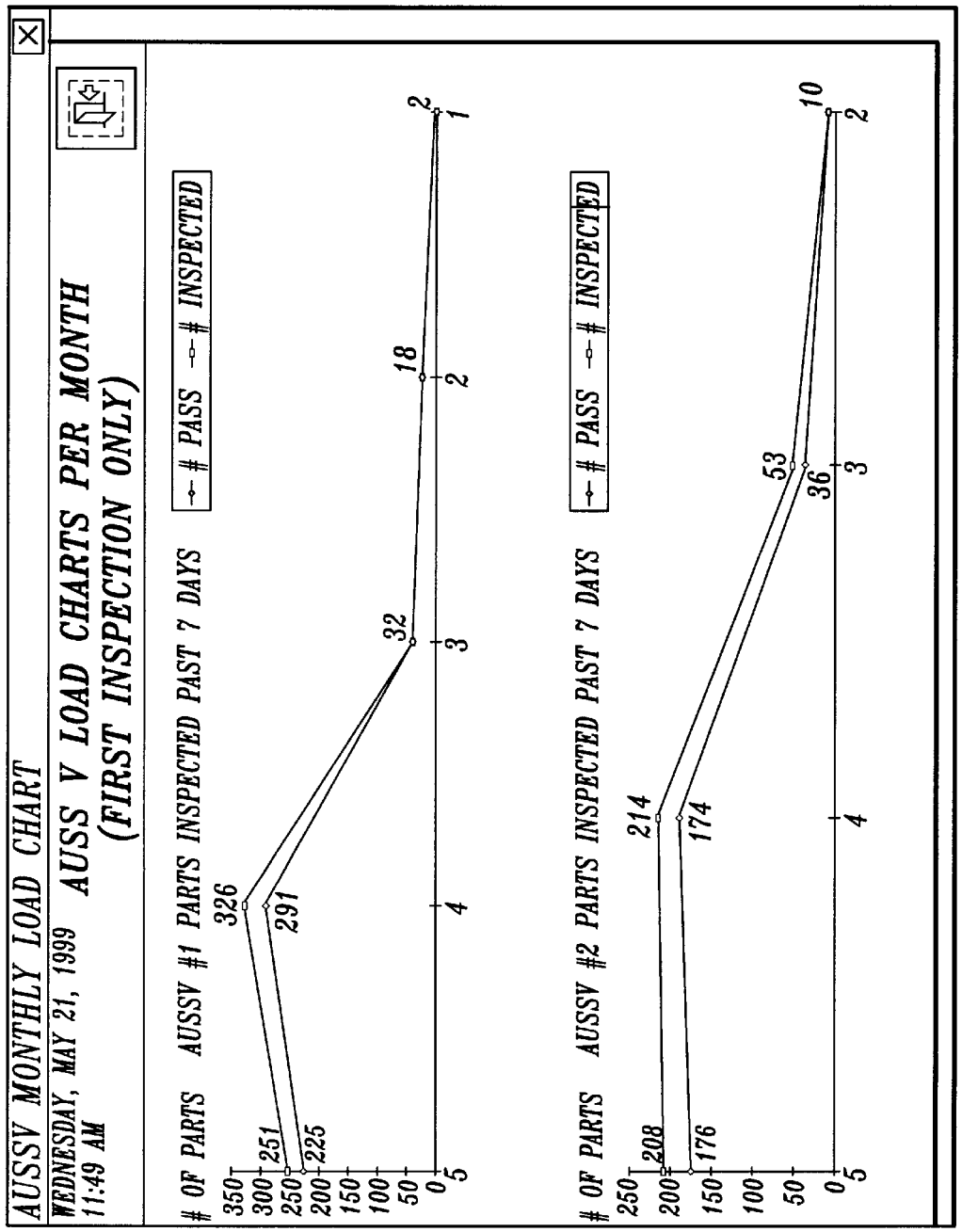
FIG. 19 is an exemplary AUSS V monthly load chart report that is displayed when a button in the MORE QUERIES and other window is selected by the user.

If the AUSS V GRAPHS LOAD CHARTS BY DAY button 450 has not been actuated, a test 508 is made to determine if the FIRST AUSS V GRAPHS LOAD CHART BY MONTH button 452 has been actuated. If the FIRST AUSS V GRAPHS LOAD CHART BY MONTH button has been actuated, an AUSS V MONTHLY LOAD CHART report is displayed. See block 510. An example of an AUSS V MONTHLY LOAD CHART report is illustrated in FIG. 19 and described below. When the AUSS V MONTHLY LOAD CHART report display is closed, the process cycles to the exit button actuated test 470.

Figure 20:
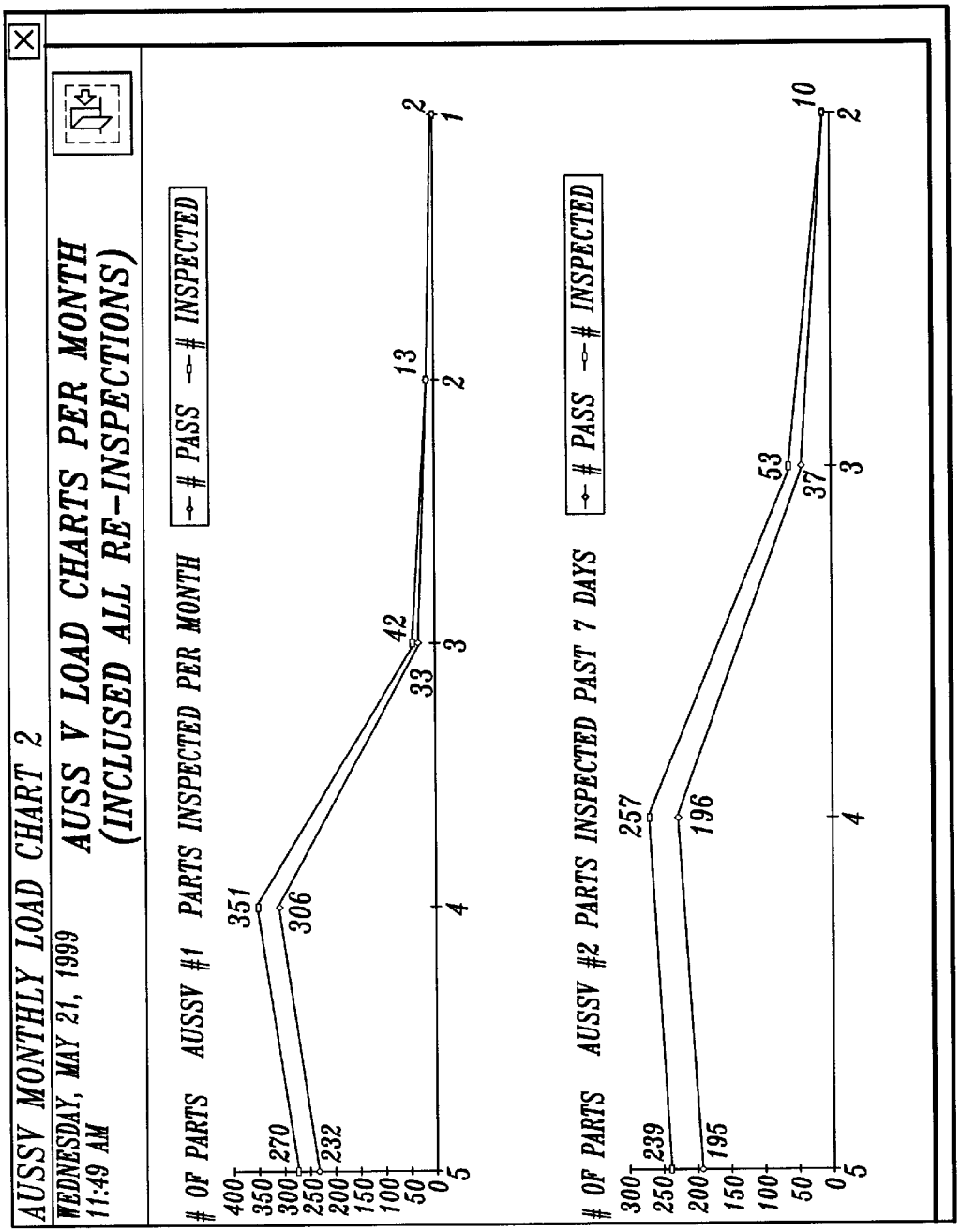
FIG. 20 is an exemplary AUSS V monthly load chart 2 report that is displayed when a button in the MORE QUERIES and other window is selected by a user.

If the FIRST AUSS V GRAPHS LOAD CHART BY MONTH button 452 has not been actuated, a test 512 is made to determine if the ALL AUSS V GRAPHS LOAD CHART BY MONTH button 454 has been actuated. If the ALL AUSS V GRAPHS LOAD CHART BY MONTH button has been actuated, an AUSS V MONTHLY LOAD CHART 2 report is displayed. See block 514. An example of an AUSS V MONTHLY LOAD CHART 2 report is illustrated in FIG. 20 and described below. When the AUSS V MONTHLY LOAD CHART 2 report display is closed, the process cycles to the exit button actuated test 470.

If the ALL AUSS V GRAPHS LOAD CHART BY MONTH button 454 has not been actuated, a test 516 is made to determine if the IMAGE TOOL button 456 has been actuated. If the IMAGE TOOL button 456 has been actuated, the IMAGE TOOL program is launched. See block 518. When the IMAGE TOOL program is closed, the process cycles to the exit button actuated test 470.

If the IMAGE TOOL button has not been actuated, a test 520 (FIG. 15D) is made to determine if the PRINT PASS BAKE % LAST 60 DAYS button 458 has been actuated. If the PRINT PASS BAKE % LAST 60 DAYS button has been actuated, a BAKE PASS PERCENTAGES report is printed. See block 522. Thereafter, the process cycles to the exit button actuated test 470. If the PRINT PASS BAKE % LAST 60 DAYS button 458 has not been actuated, a test 524 is made to determine if the PRINT 10 PART TREND 1st INSP. button 460 has been actuated. If the PRINT 10 PART TREND 1st INSP. button has been actuated, a FIRST TIME TREND report is printed. See block 526. Thereafter, the process cycles to the exit button actuated test.

If the PRINT 10 PART TREND 1st INSP. button 460 has not been actuated, a test 528 is made to determine if the PRINT 10 PART TREND ALL INSP. button 462 has been actuated. If the PRINT 10 PART TREND ALL INSP. button has been actuated, a REWORK TREND report is printed. See block 530. Thereafter, the process cycles to the exit button actuated test 470.

If the PRINT 10 PART TREND ALL INSP. button has not been actuated, a test 532 is made to determine if the PRINT AUSS V RUNS button 464 has been actuated. If the PRINT AUSS V RUNS button has been actuated, an AUSS V RUNS FOR DATE SPECIFIED report is printed. See block 534. Thereafter, the process cycles to the exit button actuated test 470. If the PRINT AUSS V RUNS button 464 has not been actuated, a test 536 is made to determine if the PRINT PASS % 1st INSP. button 466 has been actuated. If the PRINT PASS %–1st INSP. button has been actuated, a Last 60 Days of AUSS V 1st Time Inspection Results Reference From Part Number Or Current Record is printed. See block 538. Thereafter, the process cycles to the exit button actuated test 470.

If the PRINT PASS %–1st INSP. button 466 has not been actuated, a test 540 is made to determine if the PRINT PASS % ALL INSP. button 468 has been actuated. If the PRINT PASS % ALL INSP. button has been actuated, a Last 60 Days of AUSS V 1st Time Insp. Results Referenced From The Part Number On The Current Record Including Reinspections is printed. See block 542. Thereafter, or if the PRINT PASS % ALL INSP. button 468 has not been actuated, the process cycles to the exit button actuated test 470.

FIG. 16 is an example of a Global Statistics 2 report that is displayed when the GLOBAL GRAPHS PASS % 1st INSP. 60 DAYS button 446 of the MORE QUERIES and other window 432 is actuated. An exit button is located in the top-right corner of the GLOBAL STATISTICS 2 report. The GLOBAL STATISTICS 2 report contains two charts. The top chart is a bar graph that shows the 10 highest defect parts (by percentages of pass vs. total inspected) in the past 60 days. The bottom chart shows the 10 most common defect types that have been identified. Preferably, the graphed inspection pass percentages are derived from a sample of at least five composite part global records occurring in the past 60 days.

FIG. 17 is an example of a GLOBAL STATISTICS report that is displayed when the GLOBAL GRAPHS DEFECTS, ALL INSP. 60 DAYS button 448 in the MORE QUERIES and other window 432 (FIG. 15A) is actuated. An exit button is positioned at the top-right corner of the global statistics form. The Global Statistics report includes two charts. The charts display a graphical view showing the 10 highest defective composite parts in the past 60 days and highest defect types (up to 10) that have been identified.

FIG. 18 is an example of an AUSS V WEEKLY LOAD CHART report that is displayed when the AUSS V GRAPHS LOAD CHART BY DAY button 440 in the MORE QUERIES and other window 432 is actuated. An exit button is positioned at the top right corner of the AUSS V weekly load chart report. This report includes two graphs showing the inspection results for two automated ultrasonic scanning systems identified as AUSS V System 1 and AUSS V System 2 for the past week. The graphs include two lines, the upper line showing the number of parts inspected and the lower line showing the number of parts that passed the inspection. Preferably the AUSS V weekly load chart report is based solely on the number of parts inspected and does not consider the size in part square feet or the speed of inspection. As shown in FIG. 23 and described below, when the AUSS V RUN button 282 in the QA record window 188 is actuated, a report is displayed that shows the types of parts that were inspected on a given day. The AUSS V weekly load chart can be compared to the OEE record to determine if a system had been down on a particular day for maintenance or repairs.

FIG. 19 is an example of a AUSS V MONTHLY LOAD CHART report that is displayed when the 1st AUSS V GRAPHS LOAD CHART BY MONTH button 452 in the MORE QUERIES and other window 432 is actuated. An exit button is positioned at the top-right corner of the AUSS V MONTHLY LOAD CHART report. This report includes two graphs, one for the AUSS V system 1 and one for the AUSS V system 2 that show inspection loads of the past months for first time inspected parts. The graphs include two lines, the upper line shows the number of parts inspected, and the lower line shows the number of parts that passed the inspection. This report is based on the number of parts inspected and entered into the database per month.

FIG. 20 is an example of a AUSS V MONTHLY LOAD CHART 2 report that is displayed when the ALL AUSS V GRAPHS LOAD CHART BY MONTH button 454 in the MORE QUERIES and other window 432 is actuated. An exit button is positioned at the top-right corner of the AUSS V MONTHLY LOAD CHART 2 report. This report also includes two graphs, one for the AUSS V system 1 and the other for the AUSS V system 2, that show the number of parts inspected per month for the past several months, including reinspections. The graphs include two lines: the upper line shows the number of parts inspected and the lower line shows the number of parts that passed the inspection. The AUSS V MONTHLY LOAD CHART 2 report is based on the number of parts inspected and entered into the database per month.

When the values from AUSS V MONTHLY LOAD CHART 2 report (FIG. 20) are subtracted from the values in the AUSS V MONTHLY LOAD CHART report (FIG. 19), the result indicates how many composite parts were re-inspected. The percentage of rework can be determined by dividing the result of this subtraction by the total indicated in the AUSS V MONTHLY LOAD CHART 2 report. Preferably, the composite parts are not weighted according to size or inspection time.

Queries are complex filters that are designed to extract data from a table stored in a software database. Query filters quickly extract information that could be prone to human error or next to impossible to manually extract. Queries are powerful and their outputs can be used to draw graphs or exported to other spreadsheets for further evaluation. The QTS uses queries to draw graphs, print reports, and calculate percentage yield for composite parts. Since techniques for creating queries are well known to those familiar with software databases, such techniques are not described here. Rather, only the results of queries are described.

In the QA DATA RECORD window 188 (FIG. 9A), the bottom row of buttons are used for data analysis and queries of the records stored in the QTS database related to the displayed QA DATA RECORD. The PART TREND 1st INSP. button 276 causes a PART TREND 2: SELECT QUERY report to be displayed. An example of such a report is shown in FIG. 21. The PART TREND 2: SELECT QUERY report is a table that includes a number of columns—for example, Product Name, Dash #, TKR #, Date (Inspection), Pass (yes/no), AUSS V NCR #, etc. The TKR # directly referenced to the current QA DATA RECORD and all dash numbers related to the part number are displayed. If desired, the button identified by the binocular icon may be used to search for the QA DATA RECORD with the desired part number.

Actuation of the PASS % 1st INSP. <60 DAYS. button 278 of the QA DATA RECORD window 188 causes the last 60 days of first time inspection results relating to the part number of the current QA DATA RECORD to be accessed and a PERCENT: SELECT QUERY report to be displayed. An example search report is illustrated in FIG. 22. Actuation of the PASS % TOTAL <60 DAYS. button functions in a similar manner, the difference being that reinspection results as well as first time inspection results are accessed to create the PERCENT SELECT: QUERY report that is displayed.

When the AUSS V RUN. button 282 in the QA DATA RECORD window 188 (FIG. 9A) is actuated, a date search criteria window for AUSS V inspections (not shown) that requests a range of dates to search the QA DATA RECORDS for the first time pass of the AUSS V inspection opens, e.g., "DateFrom__; DateTo__." Based on the inputted dates, the query will return all part numbers within the search dates and indicate the inspection results. An example of the report produced as a result of such a query is illustrated in FIG. 23.

When the PART TREND (ALL INSP.) button 394 of the REPAIR RECORD window 358 (FIG. 11A) is actuated, a report is displayed that is similar to the report that is displayed when the PART TREND 1st INSP. button 276 of the QA record window is actuated, except that the report includes all reinspections. An example of the report that is produced when the PART TREND (ALL INSP.) button 394 is actuated, which is titled PART TREND: SELECT QUERY, is shown in FIG. 24.

When the SELECT IMAGE button 398 of the repair window 358 is actuated, a window (not shown) opens. When an image file name in appropriate form is entered, the image is displayed. The preferred image file name form is TIFF. Obviously the image must be stored on the database 18 (FIG. 1) in order to be retrieved.

When the GLOBAL PASS % ALL 1st AUSS V INSP. 60 DAYS button 434 of the MORE QUERIES and other window 432 is actuated, a report that includes the Global Statistics 2 report (FIG. 16) is displayed. The difference is that the report created when the GLOBAL PASS % ALL 1st AUSS V INSP. 60 DAYS button is actuated is tabular in form and allows all worst case parts to be reviewed or exported into a spreadsheet. An example of the report that is displayed when the GLOBAL PASS % ALL 1st AUSS V INSP. 60 DAY button is actuated, which is titled GLOBAL PERCENT FIRST: SELECT QUERY, is shown in FIG. 25.

When the GLOBAL PASS % ALL AND 1st INSP. (ENTER MONTH) button 436 of the MORE QUERIES and other window 432 is actuated, eight separate queries are launched. The month of interest is entered in number format for the second and third queries.

The first query creates a report titled GLOBAL PERCENT ALL 1ST INSP: SELECT QUERY, an example of which is shown in FIG. 26. This query samples the inspection data for all composite parts stored in the database and returns a tabular report that shows pass percentages of all first time inspections sorted by ascending part numbers.

The second and third queries are substantially the same as the first query except that the second query is for the entered month and the third query is for all inspections. Examples of the reports resulting from these queries are illustrated in FIG. 27. Examples of the reports resulting from the fourth, fifth, and sixth queries are displayed in FIG. 28. These reports show first time inspections by month and line number (Production Model) of finished assemblies. Interim inspections of subcomponents for the final assembly are not considered. FIG. 29 illustrates the reports resulting from the seventh and eighth queries. These reports show the results of first inspections and all inspections by the month. The seventh query report equals the sum of the fourth, fifth, and sixth queries report.

When the LAST 60 DAYS AUTOCLAVE BAKE PASS % button 438 of the MORE QUERIES and other window 432 (FIG. 15A) is actuated, a query that returns a report of the pass percentage of autoclave runs. An example of the report that is produced, which is titled SELECT QUERY: PERCENT BAKE, is illustrated in FIG. 30. Preferably, the bake number is referenced to the last 60 days from the current form date.

When the AUSS V LOAD CHART BY DAY button 440 of the MORE QUERIES and other window 432 (FIG. 15A) is actuated, a query of AUSS V system 1 and 2 inspection loads for a past week occurs and a load chart (not shown) is displayed. This query is based on the number of parts inspected and does not take into the consideration the size of the parts in square feet or inspection speed. As noted above, the AUSS V RUN button 282 in the QA DATA RECORD window 188 (FIG. 9A) may be used to launch a query to determine what types of parts were run for a given day. The report resulting from this query may be compared to the OEE record to determine if a system had been down on that day for maintenance and repairs.

When the MACHINE WEEKLY PASS % button 442 of the MORE QUERIES and other window 432 is actuated, a query of the AUSS V system 1 and AUSS V system 2 inspection pass percentages for the past week occurs and a report of the type illustrated in FIG. 31 titled AUSS #1 WEEKLY PASS PERCENTAGES: SELECT QUERY and AUSS #2 WEEKLY PASS PERCENTAGES: SELECT QUERY are produced. Examples of these reports are shown in FIG. 31.

When the REJECTIONS PAST 60 DAYS button 444 of the MORE QUERIES and other window 432 is actuated, a query is launched and a report of the type shown in FIG. 32 is displayed. The report shows part rejections that occurred in the past 60 days. The report includes information such as date, NCR #, TKR #, INSP. #, LOG #, PART #, # of Defects and other information, all in tabular form.

Obviously the foregoing description and accompanying figures are to be taken as exemplary and not limiting of the types of available queries and reports. Other queries may be built provided that the necessary inspection data is entered into the database through the QA DATA RECORD window, REPAIR RECORD window, or some other newly designed record window. Also, if necessary, additional windows designed to accommodate associations with new queries can be constructed.

Reports are directly tied to the query buttons described above and the QTS enables the results of the queries to be displayed in a readable format as graphs and tables. Preferably, as shown and described, the report information is referenced from the QA DATA RECORD window or REPAIR RECORD window. The references in these windows help save time and eliminate operator input error. Reports may be tailored to fit a need if all of the necessary information is available via the QA DATA RECORD and REPAIR RECORD windows.

Turning now to the print buttons located at the bottom of the MORE QUERIES and other window 432, when the PRINT PASS BAKE % LAST 60 DAYS button 458 is actuated, a report of the autoclave bake pass percentages for the last 60 days is printed out. A user can use this report to correlate problems with the autoclave cycle with low percentages. When the PRINT 10 PART TREND 1st INSP. button 460 is actuated, the data that is displayed in the First Time Trend report (FIG. 12) is printed out. When the PRINT 10 PART TREND ALL INSP. button 462 is actuated, the data that is displayed in the Rework Trend report (FIG. 14) is printed out. When the PRINT AUSS V RUNS button 464 is actuated, the AUSS V runs for a specified date are printed out. When the PRINT PASS %–1st INSP. button 466 is actuated, a report of the last 60 days of AUSS V first time inspection results referenced from the part number on the current QA DATA RECORD is printed out. When the PRINT PASS % ALL INSP. button 468 is actuated, a report of the last 60 days of all AUSS V inspection results referenced from the part number on the current QA DATA RECORD including re-inspections that indicate the success of repairs to the composite parts is printed out.

The easiest way to search for information is to select the button identified with the binocular icon in the QA DATA RECORD window. As noted above, actuating the binocular button will call a search engine that prompts for a search string and a direction to search, i.e., either up or down. The search string may include a TKR #, NCR #, bake #, image #, and part number. Because a user will most often begin at the last record entered, most searches will be directed upwards.

FIG. 33 is an exemplary embodiment of a scan image that has been edited to include data associated with the composite part. As described above, the location of defects are explicitly identified on the edited scan image of the composite part, and the date, type, and alphanumeric identifier for each deficiency are inserted so as to be clearly visible.

As noted above, preferably, the invention is implemented by using commercially available software modules to accomplish the various major functions of the invention. Examples of suitable software modules produced by the Microsoft Corporation, Redmond, Washington, are as follows:

| SOFTWARE MODULE | VERSION | USE |
| --- | --- | --- |
| Microsoft Access 97 | Ver. 8.0.3512 | QTS database engine |
| Microsoft Paint | Ver. 4.00.950 | Standard images (BMP) |

-continued

| SOFTWARE MODULE | VERSION | USE |
| --- | --- | --- |
| Microsoft Photo Editor | Ver. 96101200 | Camera images of core (JPG) |
| Microsoft Graph | Ver. 8.0 | Trend graphs |
| Microsoft Word | Ver. 8.0 | Help document viewer |

In addition to assembled composite parts, obviously the invention can be used with scan images of the components for a composite part. The invention can also be used with scan images of composite parts in situ, as opposed to during manufacture, if desired.

While the preferred embodiment of the invention has been illustrated and described, it will be appreciated that various changes can be made therein without departing from the spirit and scope of the invention. For example, the sequences shown in the functional flow diagrams illustrated in FIGS. 8B, 9B, 9C, 11B, 15B, 15C, and 15D should be taken as exemplary and not limiting. Further, these diagrams per se should be taken as exemplary, not limiting. Likewise, the window interfaces shown in FIGS. 8A, 9A, 11A, and 15A should be taken as exemplary, not limiting, as should the various report displays shown in the drawings. Hence, within the scope of the appended claims it is to be understood that the invention can be practiced otherwise than as specifically described herein.

The embodiments of the invention in which an exclusive property or privilege is claimed are defined as follows:

1. A method of providing nondestructive inspection (NDI) and other information about manufactured parts to a crew building the part and others, said computer-implementable method comprising:

gathering NDI information about parts as they are manufactured, wherein gathering NDI information about the parts comprises ultrasonically scanning the parts for defects and producing image data of at least one part that is ultrasonically scanned;

gathering other information about the parts, including repair information, part record and trend information;

linking the gathered NDI and other information, including repair information, part record and trend information, and image data, about the parts;

storing the linked, gathered NDI and other information, including repair information, part record and trend information, and image data, about the parts in a database;

at a user's request, selectively deriving information about the parts from the information about the parts stored in the database; and displaying reports based on the derived information.

2. The method claimed in claim 1, wherein gathering NDI information about parts as they are manufactured comprises ultrasonically scanning the parts for defects and producing at least one scanned image of each part that is ultrasonically scanned.

3. The method claimed in claim 2, wherein gathering NDI information about parts as they are manufactured also includes editing the scanned images of the parts.

4. The method claimed in claim 3, wherein gathering other information about the parts, including repair information, includes displaying a QA DATA RECORD window, said QA DATA RECORD window including boxes for QA personnel to enter data about the parts.

5. The method claimed in claim 4, wherein gathering other information about parts, including repair information, includes displaying a REPAIR RECORD window, said REPAIR RECORD window including boxes for repair personnel to enter data about the parts.

6. The method claimed in claim 5, wherein the QA DATA RECORD window includes an actuatable button that when actuated causes said REPAIR RECORD window to be displayed.

7. The method claimed in claim 6, wherein said QA window includes actuatable buttons that when actuated cause the selective deriving of information about the parts from the information about the parts stored in the database and the displaying of reports based on the derived information.

8. The method claimed in claim 7, wherein said repair window also includes actuatable buttons that when actuated cause the selective deriving of information about the parts from the information about the parts stored in the database and the displaying of reports based on the derived information.

9. The method claimed in claim 8 including a MORE QUERIES and other window that includes actuatable buttons that when actuated cause the selective deriving of information about the parts from the information about the parts stored in the database and the displaying of reports based on the derived information.

10. The method claimed in claim 9, wherein said QA DATA RECORD window includes a MORE QUERIES button that when actuated causes said MORE QUERIES and other window to be displayed.

11. The method claimed in claim 1, wherein gathering other information about parts, including repair information, includes displaying a REPAIR RECORD window, said REPAIR RECORD window including boxes for repair personnel to enter data about the parts.

12. The method claimed in claim 11, wherein said repair window includes actuatable buttons that when actuated cause the selective deriving of information about the parts from the information about the parts stored in the database and the displaying of reports based on the derived information.

13. The method claimed in claim 1 including a MORE QUERIES and other window that includes actuatable buttons that when actuated cause the selective deriving of information about the parts from the information about the parts stored in the database and the displaying of reports based on the derived information.

14. A computer-readable medium having computer-executable instructions for carrying out the method recited in any of claims 1–13.

15. A quality tracking system for providing nondestructive inspection (NDI) information about manufactured parts to a crew building the parts and others comprising:

an NDI system for producing NDI information about manufactured parts, wherein the NDI information about the parts comprises data for at least one image of each part that is ultrasonically scanned;

at least one computer for gathering other information about the manufactured parts, including repair information, part record and trend information, linking the NDI information to the part record and trend information, repair information and image data, and producing reports;

a database for storing the linked information obtained from said NDI system and said at least one computer; and a network for coupling said NDI system, said database, and said at least one computer system together.

16. The quality tracking system claimed in claim 15, wherein said NDI system is an ultrasonic scanning system, said ultrasonic scanning image system producing at least one scan image of each part that is scanned, said scan images stored in said database.

17. The quality tracking system claimed in claim 16, wherein the at least one computer has a user interface that includes a QA DATA RECORD window, said QA DATA RECORD window including boxes for QA personnel to enter said other information about the manufactured parts.

18. The quality tracking system claimed in claim 17, wherein the user interface of the at least one computer also includes a REPAIR RECORD window, said REPAIR RECORD window including boxes for repair personnel to enter repair information about the manufactured parts.

19. The quality tracking system claimed in claim 18, wherein the QA DATA RECORD window includes an actuatable button that when actuated causes said REPAIR RECORD window to be displayed.

20. The quality tracking system claimed in claim 19, wherein said QA DATA RECORD window includes other actuatable elements that when actuated causes said quality tracking system to selectively derive information about parts from the information stored in the database and display reports based on the derived information.

21. The quality tracking system claimed in claim 20, wherein said REPAIR RECORD window includes other actuatable buttons that when actuated cause said quality tracking system to selectively derive information about the parts from the information about the parts stored in the database and display reports based on the derived information.

22. The quality tracking system claimed in claim 21, wherein the user interface of said at least one computer also includes a MORE QUERIES and other window that includes actuatable buttons that when actuated cause said quality tracking system to selectively derive information about the parts from the information about the parts stored in the database and display reports based on the derived information.

23. The quality tracking system claimed in claim 22, wherein the MORE QUERIES and other window is displayed when a actuatable button in said QA window is actuated.

24. The quality tracking system of claim 15, wherein said at least one computer has a user interface that includes a REPAIR WINDOW, said REPAIR WINDOW including boxes for repair personnel to enter repair information.

25. The quality tracking system claimed in claim 24, wherein said REPAIR RECORD window includes other actuatable buttons that when actuated cause said quality tracking system to selectively derive information about the parts from the information about the parts stored in the database and display reports based on the derived information.

26. The quality tracking system of claim 15, wherein said at least one computer has a user interface that includes a MORE QUERIES and other window that includes actuatable buttons that when actuated cause said quality tracking system to selectively derive information about the parts from the information about the past stored in the database and display reports based on the derived information.

* * * * *

UNITED STATES PATENT AND TRADEMARK OFFICE
CERTIFICATE OF CORRECTION

PATENT NO. : 6,549,820 B1
DATED : April 15, 2003
INVENTOR(S) : R.A. Barrett et al.

It is certified that error appears in the above-identified patent and that said Letters Patent is hereby corrected as shown below:

Title page,
Item [75], Inventors, "Seattle, WA" should read -- Udall, KS --

Column 25,
Line 20, "claim 8" should read -- claim 8, --
Line 41, "claim 1" should read -- claim 1, --

Column 26,
Line 24, "when actuated causes" should read -- when actuated cause --
Line 44, "other window is" should read -- other window are --
Line 45, "a actuatable" should read -- an actuatable --
Line 63, "the past stored" should read -- the parts stored --

Signed and Sealed this

Sixteenth Day of December, 2003

JAMES E. ROGAN
*Director of the United States Patent and Trademark Office*